United States Patent
Nettekoven et al.

(10) Patent No.: US 7,432,255 B2
(45) Date of Patent: Oct. 7, 2008

(54) 1H-INDOL-5-YL-PIPERAZIN-1-YL-METHANONE DERIVATIVES

(75) Inventors: Matthias Heinrich Nettekoven, Grenzach-Wyhlen (DE); Olivier Roche, Folgensbourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/796,026

(22) Filed: Apr. 26, 2007

(65) Prior Publication Data
US 2007/0270423 A1 Nov. 22, 2007

(30) Foreign Application Priority Data
May 16, 2006 (EP) .................. 06113998

(51) Int. Cl.
*A61K 31/55* (2006.01)
*A61K 31/496* (2006.01)
*C07D 209/08* (2006.01)

(52) U.S. Cl. .............. 514/217.05; 514/228.2; 514/235.8; 514/253.09; 514/254.09; 540/598; 544/62; 544/121; 544/364; 544/373

(58) Field of Classification Search ........... None
See application file for complete search history.

(56) References Cited

U.S. PATENT DOCUMENTS

| 4,598,089 | A | 7/1986 | Hadvary et al. |
|---|---|---|---|
| 4,931,463 | A | 6/1990 | Barbier et al. |
| 4,983,746 | A | 1/1991 | Barbier et al. |
| 5,175,186 | A | 12/1992 | Barbier et al. |
| 5,246,960 | A | 9/1993 | Barbier et al. |
| 5,274,143 | A | 12/1993 | Ramig et al. |
| 5,399,720 | A | 3/1995 | Karpf et al. |
| 5,420,305 | A | 5/1995 | Ramig et al. |
| 6,004,996 | A | 12/1999 | Shah et al. |

FOREIGN PATENT DOCUMENTS

| EP | 185 359 | 6/1986 |
|---|---|---|
| EP | 189 577 | 8/1986 |
| EP | 443 449 | 8/1991 |
| EP | 524 495 | 1/1993 |
| WO | WO 99/34786 | 7/1999 |
| WO | WO 00/09122 | 2/2000 |
| WO | WO 00/09123 | 2/2000 |
| WO | WO 00/58293 | 10/2000 |
| WO | WO 01/74773 A2 | 10/2001 |
| WO | WO 01/74814 A1 | 10/2001 |
| WO | WO 02/47145 A1 | 6/2002 |
| WO | WO 2005/123716 A1 | 12/2005 |
| WO | WO 2006/077024 A1 | 7/2006 |
| WO | 2007/115938 | * 10/2007 |

OTHER PUBLICATIONS

Burks in Johnson L.R. ed., Physiology of the Gastrointestinal Tract, Raven Press, NY, pp. 211-242 (1994).
Leurs et al., Br J. Pharmacol., 102, pp. 179-185 (1991).
Raithel et al., Int. Arch. Allergy Immunol., 108, pp. 127-133 (1995).
Panula et al., Proc. Natl. Acad. Sci. USA, 81, pp. 2572-2576 (1984).
Inagaki et al., J. Comp. Neurol., 273, pp. 283-300 (1988).
Arrang et al., Nature, 302, pp. 832-837 (1983).
Arrang et al., Neuroscience, 23, pp. 149-157 (1987).
Clapham et al., Br. J. Pharmacol., 107, pp. 919-923 (1992).
Blandina et al. in The Histamine H3 Receptor (Leurs, R.L. and Timmermann, H. eds, pp. 27-40 (1998) Elsevier, Amsterdam, The Netherlands.
Masaki et al., Endocrinol., 144, pp. 2741-2748 (2003).
Hancock et al., European J. of Pharmacol., 487, pp. 183-197 (2004).
Timmermann, J. Med. Chem., 33, pp. 4-11 (1990).
Takahashi et al., J. Pharmacol. Exp. Therapeutics, 307, pp. 213-218 (2003).
Cheng., Biochem Pharmacol, 22, pp. 3099-3108 (1973).

* cited by examiner

*Primary Examiner*—Emily Bernhardt
(74) *Attorney, Agent, or Firm*—George W. Johnston; Dennis P. Tramaloni; Brian C. Remy

(57) ABSTRACT

The present invention relates to compounds of formula I and their pharmaceutically acceptable salts wherein in formula I is:

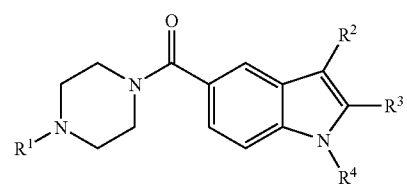

wherein $R^1$ to $R^4$ are as defined in the description and claims. The compounds of the present invention are useful for the treatment and/or prevention of diseases which are associated with the modulation of histamine 3 (H3) receptors.

23 Claims, No Drawings

1H-INDOL-5-YL-PIPERAZIN-1-YL-METHANONE DERIVATIVES

PRIORITY TO RELATED APPLICATION(S)

This application claims the benefit of European Patent Application No. 06113998.6, filed May 16, 2006, which is hereby incorporated by reference in its entirety.

BACKGROUND OF THE INVENTION

The present invention is concerned with novel 1H-indol-5-yl-piperazin-1-yl-methanone derivatives, their manufacture, pharmaceutical compositions containing them and their use as antagonists and/or inverse agonists at the histamine 3 receptor (H3 receptor).

Histamine (2-(4-imidazolyl)ethylamine) is one of the aminergic neurotransmitters which is widely distributed throughout the body, e. g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tubero-mammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors. H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs RL and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

It is therefore an object of the present invention to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In particular, the present invention relates to the compounds of formula I which includes all pharmaceutically acceptable salts thereof, wherein formula I is:

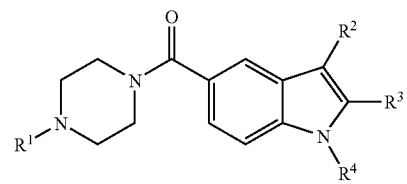

wherein:
  $R^1$ is lower alkyl or cycloalkyl;
  $R^2$ is hydrogen or halogen;
  $R^3$ is hydrogen or lower alkyl; and
  $R^4$ is —$(CR^5R^6)_m$—$NR^7R^8$ or —$(CR^9R^{10})_n$-heterocyclyl,
wherein:
  (a) $R^5$ is hydrogen or lower alkyl;
  (b) $R^6$ is hydrogen or lower alkyl;
  (c) $R^7$ and $R^8$ independently from each other are selected from the group consisting of:
    (1) lower alkyl,
    (2) phenyl optionally substituted by lower alkyl,
    (3) lower phenylalkyl, and
    (4) lower hydroxyalkyl; or alternatively
    $R^7$ and $R^8$ together with the nitrogen atom to which they are attached form a 3-, 4-, 5-, 6- or 7-membered saturated heterocyclic ring optionally containing a further heteroatom of oxygen or sulfur, said heterocyclic ring being optionally substituted by lower alkyl;
  (d) $R^9$ is hydrogen or lower alkyl;
  (e) $R^{10}$ is hydrogen or lower alkyl;
  (f) said heterocyclyl is a N-heterocyclic ring selected from the group consisting of pyrrolidine, pyrrolidin-2-one, piperidine and morpholine, wherein the nitrogen atom of the N-heterocyclic ring is substituted by a substituent selected from the group consisting of:
    (1) lower alkyl,
    (2) cycloalkyl,
    (3) lower phenylalkyl,
    (4) lower cyanoalkyl,
    (5) lower halogenalkyl,
    (6) lower alkoxyalkyl, (7) phenyl optionally substituted by one to three substituents selected from the group consisting of lower alkyl, lower alkoxy, lower halogenalkyl and halogen, and (8) —COOR$^{11}$; wherein R$^{11}$ is lower alkyl;

(g) m is 2 or 3, and (h) n is 0, 1, 2 or 3.

The compounds of formula I are antagonists and/or inverse agonists at the histamine 3 receptor (H3 receptor). Such antagonists/inverse agonists are useful as therapeutically active substances, particularly in the treatment and/or prevention of diseases which are associated with the modulation of H3 receptors, such as (but not limited to) obesity, metabolic syndrome (syndrome X), and other eating disorders.

DETAILED DESCRIPTION OF THE INVENTION

In the present description the term "alkyl", alone or in combination with other groups, refers to a branched or straight-chain monovalent saturated aliphatic hydrocarbon radical of one to twenty carbon atoms. In certain preferred embodiments the alkyl is one to sixteen carbon atoms, more preferably one to ten carbon atoms.

The term "lower alkyl" or "$C_1$-$C_7$-alkyl", alone or in combination, signifies a straight-chain or branched-chain alkyl group with 1 to 7 carbon atoms. In certain preferred embodiments, the lower akyl or $C_1$-$C_7$-alkyl, is a straight or branched-chain alkyl group with 1 to 6 carbon atoms and more preferably a straight or branched-chain alkyl group with 1 to 4 carbon atoms. Examples of straight-chain and branched $C_1$-$C_7$ alkyl groups are methyl, ethyl, propyl, isopropyl, butyl, isobutyl, tert.-butyl, the isomeric pentyls, the isomeric hexyls and the isomeric heptyls, preferably methyl and ethyl and more preferably methyl.

The term "lower alkenyl" or "$C_{2-7}$-alkenyl", alone or in combination, signifies a straight-chain or branched hydrocarbon radical comprising an olefinic bond and up to 7 carbon atoms. In certain preferred embodiments, the lower alkenyl or $C_{2-7}$-alkenyl contains preferably up to 6, and more preferably up to 4 carbon atoms. Examples of lower alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7 carbon atoms. In certain preferred embodiments, the lower alkinyl or $C_{2-7}$-alkinyl contains up to 6, and more preferably up to 4 carbon atoms. Examples of alkinyl groups are ethinyl, 1-propinyl, or 2-propinyl. A preferred example is 2-propinyl.

The term "cycloalkyl" or "$C_3$-$C_7$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "alkoxy" or "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy, and more preferably methoxy.

The term "lower alkoxyalkyl" or "$C_1$-$C_7$-alkoxy-$C_1$-$C_7$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "halogen" refers to fluorine, chlorine, bromine and iodine, with fluorine, chlorine and bromine being preferred.

The term "lower halogenalkyl" or "halogen-$C_1$-$C_7$-alkyl" refers to lower alkyl groups as defined above wherein at least one of the hydrogen atoms of the lower alkyl group is replaced by a halogen atom. In certain preferred embodiments, the halogen atom is fluoro or chloro, and most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower phenylalkyl" or "phenyl-$C_{1-7}$-alkyl" refers to lower alkyl groups as defined above wherein at least one of the hydrogen atoms of the lower alkyl group is replaced by a phenyl group. Preferred lower phenylalkyl groups are benzyl or phenethyl.

The term "lower cycanoalkyl" or "cyano-$C_{1-7}$-alkyl" refers to lower alkyl groups as defined above wherein at least one of the hydrogen atoms of the lower alkyl group is replaced by a cyano group. A preferred lower cyanoalkyl group is cyanomethyl.

The term "heterocyclyl" in general refers to a saturated or partly unsaturated ring which can comprise one, two or three atoms selected from nitrogen, oxygen and/or sulphur. Examples of heterocyclyl rings include aziridinyl, azetidinyl, pyrrolidinyl, piperidinyl, azepinyl, piperazinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, oxiranyl, oxetanyl, dihydropyranyl, tetrahydropyranyl and thiomorpholinyl.

The term "N-heterocyclic ring" refers to heterocyclyl groups containing at least one nitrogen atom. Examples of "N-heterocyclic rings" include aziridinyl, azetidinyl, pyrrolidinyl, piperidinyl, azepinyl, piperazinyl, morpholinyl and thiomorpholinyl, but also include rings containing additionally a carbonyl group such as pyrrolidin-2-one. Preferred "N-heterocyclic rings" are pyrrolidinyl, piperidinyl, morpholinyl and pyrrolidin-2-one.

The term "form a 3-, 4-, 5-, 6- or 7-membered saturated heterocyclic ring optionally containing a further heteroatom selected from oxygen or sulfur" refers to a N-heterocyclic ring, which may optionally contain a further oxygen or sulfur atom, such as aziridinyl, azetidinyl, pyrrolidinyl, oxazolidinyl, isoxazolidinyl, thiazolidinyl, isothiazolidinyl, piperidinyl, morpholinyl, thiomorpholinyl, or azepanyl. The heterocyclic ring may be unsubstituted or substituted by lower alkyl.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to) the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space and have one or more asymmetric carbon atoms are termed "stereoisomers." Stereoisomers that are not mirror images of one another are termed "diastereoisomers", and stereoisomers that are non-superimposable mirror images are termed "enantiomers", or sometimes optical isomers.

In detail, the present invention relates to the compounds of formula I and all pharmaceutically acceptable salts thereof, wherein formula I is:

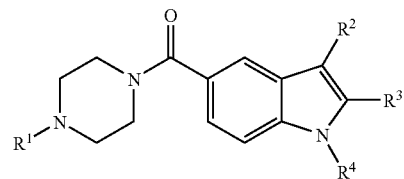

wherein:
  $R^1$ is lower alkyl or cycloalkyl;
  $R^2$ is hydrogen or halogen;
  $R^3$ is hydrogen or lower alkyl; and
  $R^4$ is —$(CR^5R^6)_m$—$NR^7R^8$ or —$(CR^9R^{10})_n$-heterocyclyl,
wherein:
  (a) $R^5$ is hydrogen or lower alkyl;
  (b) $R^6$ is hydrogen or lower alkyl;
  (c) $R^7$ and $R^8$ independently from each other are selected from the group consisting of:
    (1) lower alkyl,
    (2) phenyl optionally substituted by lower alkyl,
    (3) lower phenylalkyl, and
    (4) lower hydroxyalkyl; or alternatively
    $R^7$ and $R^8$ together with the nitrogen atom to which they are attached form a 3-, 4-, 5-, 6- or 7-membered saturated heterocyclic ring optionally containing a further heteroatom of oxygen or sulfur, said heterocyclic ring being optionally substituted by lower alkyl;
  (d) $R^9$ is hydrogen or lower alkyl;
  (e) $R^{10}$ is hydrogen or lower alkyl;
  (f) said heterocyclyl is a N-heterocyclic ring selected from the group consisting of pyrrolidine, pyrrolidin-2-one, piperidine and morpholine, wherein the nitrogen atom of the N-heterocyclic ring is substituted by a substituent selected from the group consisting of:
    (1) lower alkyl,
    (2) cycloalkyl,
    (3) lower phenylalkyl,
    (4) lower cyanoalkyl,
    (5) lower halogenalkyl,
    (6) lower alkoxyalkyl,
    (7) phenyl optionally substituted by one to three substituents selected from the group consisting of lower alkyl, lower alkoxy, lower halogenalkyl and halogen, and
    (8) —$COOR^{11}$; wherein $R^{11}$ is lower alkyl;
  (g) m is 2 or 3, and
  (h) n is 0, 1, 2 or 3.

In one particular embodiment, $R^1$ is lower alkyl, $R^2$ is hydrogen; and $R^3$ is hydrogen.

In another particular embodiment, $R^1$ is lower alkyl, $R^2$ is hydrogen; and $R^3$ is lower alkyl.

In another particular embodiment, $R^1$ is lower alkyl, $R^2$ is halogen; and $R^3$ is hydrogen.

In another particular embodiment, $R^1$ is lower alkyl, $R^2$ is halogen; and $R^3$ is lower alkyl.

In another particular embodiment, $R^1$ is cycloalkyl, $R^2$ is hydrogen; and $R^3$ is hydrogen.

In another particular embodiment, $R^1$ is cycloalkyl, $R^2$ is hydrogen; and $R^3$ is lower alkyl.

In another particular embodiment, $R^1$ is cycloalkyl, $R^2$ is halogen; and $R^3$ is hydrogen.

In another particular embodiment, $R^1$ is cycloalkyl, $R^2$ is halogen; and $R^3$ is lower alkyl.

Preferred are the compounds of formula I according to the present invention, wherein $R^4$ is
—$(CR^9R^{10})_n$-heterocyclyl and wherein:
n is 0, 1, 2 or 3;
$R^9$ is hydrogen or lower alkyl;
$R^{10}$ is hydrogen or lower alkyl; and
the heterocyclyl is a N-heterocyclic ring selected from the group consisting of: pyrrolidine, pyrrolidin-2-one, piperidine and morpholine, wherein the nitrogen atom is substituted by a group selected from the group consisting of: (1) lower alkyl, (2) cycloalkyl, (3) lower phenylalkyl, (4) lower cyanoalkyl, (5) lower halogenalkyl, (6) lower alkoxyalkyl, (7) unsubstituted phenyl or phenyl substituted by one to three groups selected from the group consisting of lower alkyl, lower alkoxy, lower halogenalkyl and halogen, and (8) —$COOR^{11}$; wherein $R^{11}$ is lower alkyl.

A preferred group of compounds of formula I according to the invention are those, wherein $R^4$ is —$(CR^9R^{10})_n$-heterocyclyl and wherein:
n is 0, 1, 2 or 3;
$R^9$ is hydrogen or lower alkyl;
$R^{10}$ is hydrogen or lower alkyl; and
the heterocyclyl is a N-heterocyclic ring selected from the group consisting of pyrrolidine and pyrrolidin-2-one, wherein the nitrogen atom is substituted by a group selected from the group consisting of: (1) lower alkyl, (2) cycloalkyl, (3) lower phenylalkyl, (4) lower cyanoalkyl, (5) lower halogenalkyl, (6) lower alkoxyalkyl, (7) unsubstituted phenyl or phenyl substituted by one to three groups consisting of lower alkyl, lower alkoxy, lower halogenalkyl and halogen, and (8) —$COOR^{11}$; wherein $R^{11}$ is lower alkyl.

Especially preferred are compounds of formula I according to the invention, wherein $R^4$ is —$(CR^9R^{10})_n$-heterocyclyl and wherein:
n is 0, 1, 2 or 3;
$R^9$ is hydrogen or lower alkyl;
$R^{10}$ is hydrogen or lower alkyl; and
the heterocyclyl is pyrrolidin-3-yl, wherein the nitrogen atom is substituted by a group selected from the group consisting of: (1) lower alkyl, (2) cycloalkyl, (3) lower phenylalkyl, (4) lower cyanoalkyl, (5) lower halogenalkyl, (6) lower alkoxyalkyl, (7) unsubstituted phenyl or phenyl substituted by one to three groups selected from the group consisting of lower alkyl, lower alkoxy, lower halogenalkyl and halogen, and (8) —$COOR^{11}$; wherein $R^{11}$ is lower alkyl.

Another group of preferred compounds of formula I according to the invention includes those, wherein $R^4$ is —$(CR^9R^{10})_n$-heterocyclyl and wherein:
n is 0, 1, 2 or 3;
$R^9$ is hydrogen or lower alkyl;
$R^{10}$ is hydrogen or lower alkyl; and
the heterocyclyl is a N-heterocyclic ring which is piperidine or morpholine, wherein the nitrogen atom is substituted by a group selected from the group consisting of: (1) lower alkyl, (2) cycloalkyl, (3) lower phenylalkyl, (4) lower cyanoalkyl, (5) lower halogenalkyl, (6) lower alkoxyalkyl, (7) unsubstituted phenyl or phenyl substituted by one to three groups selected from the group consisting of lower alkyl, lower alkoxy, lower halogenalkyl and halogen, and (8) —$COOR^{11}$; wherein $R^{11}$ is lower alkyl.

Especially preferred are compounds of formula I according to the invention, wherein $R^4$ is —$(CR^9R^{10})_n$-heterocyclyl and wherein:
n is 0, 1, 2 or 3;
$R^9$ is hydrogen or lower alkyl;
$R^{10}$ is hydrogen or lower alkyl; and
the heterocyclyl is piperidin-3-yl, wherein the nitrogen atom is substituted by a group selected from the group consisting of: (1) lower alkyl, (2) cycloalkyl, (3) lower phenylalkyl, (4) lower cyanoalkyl, (5) lower halogenalkyl, (6) lower alkoxyalkyl, (7) unsubstituted phenyl or phenyl substituted by one to three groups selected from the group consisting of lower alkyl, lower alkoxy, lower halogenalkyl and halogen, and (8) —$COOR^{11}$; wherein $R^{11}$ is lower alkyl.

Furthermore, compounds of formula I according to the present invention are preferred, wherein $R^4$ is —$(CR^9R^{10})_n$-heterocyclyl and wherein the nitrogen atom of the heterocyclyl group is substituted by a group selected from the group consisting of: (1) lower alkyl, (2) cycloalkyl, (3) lower phenylalkyl, (4) lower cyanoalkyl, (5) lower halogenalkyl, (6) lower alkoxyalkyl, (7) unsubstituted phenyl or phenyl substituted by one to three groups selected from the group consisting of lower alkyl, lower alkoxy, lower halogenalkyl and halogen.

Preferably, $R^9$ and $R^{10}$ are hydrogen.

The integer n has the significances 0, 1, 2 or 3. Preferably, n is 0, 1 or 2. More preferably, n is 0 or 1.

Further preferred compounds of formula I according to the present invention are those, wherein:
$R^4$ is —$(CR^5R^6)_m$—$NR^7R^8$ and wherein m is 2 or 3;
$R^5$ is hydrogen or lower alkyl;
$R^6$ is hydrogen or lower alkyl;
$R^7$ and $R^8$ independently from each other are selected from the group consisting of: (1) lower alkyl, (2) unsubstituted phenyl or phenyl substituted by lower alkyl, (3) lower phenylalkyl and (4) lower hydroxyalkyl, or
$R^7$ and $R^8$ together with the nitrogen atom to which they are attached form a 3-, 4-, 5-, 6- or 7-membered saturated heterocyclic ring optionally containing a further heteroatom selected from oxygen or sulfur, said heterocyclic ring being unsubstituted or substituted by lower alkyl.

One group of preferred compounds of formula I according to the invention includes those, wherein:
$R^4$ is —$(CR^5R^6)_m$—$NR^7R^8$ and wherein m is 2 or 3;
$R^5$ is hydrogen or lower alkyl;
$R^6$ is hydrogen or lower alkyl; and
$R^7$ and $R^8$ independently from each other are selected from the group consisting of lower alkyl, unsubstituted phenyl or phenyl substituted by lower alkyl, lower phenylalkyl and lower hydroxyalkyl.

Another group of preferred compounds of formula I according to the invention are those, wherein:
$R^4$ is —$(CR^5R^6)_m$—$NR^7R^8$ and wherein m is 2 or 3, $R^5$ and $R^6$ are hydrogen and $R^7$ and $R^8$ together with the nitrogen atom to which they are attached form a 3-, 4-, 5-, 6- or 7-membered saturated heterocyclic ring optionally containing a further heteroatom selected from oxygen or sulfur, said heterocyclic ring being unsubstituted or substituted by lower alkyl.

The integer m has the significances 2 or 3. Preferably, m is 2.

$R^5$ and $R^6$ are preferably hydrogen.

More preferably, compounds of formula I according to the invention are those, wherein $R^4$ is —$(CR^5R^6)_m$—$NR^7R^8$ and wherein m is 2 or 3, $R^5$ and $R^6$ are hydrogen and $R^7$ and $R^8$ together with the nitrogen atom to which they are attached form a heterocyclic ring selected from the group consisting of aziridine, azetidine, pyrrolidine, piperidine, azepane, morpholine and thiomorpholine, said heterocyclic ring being unsubstituted or substituted by lower alkyl.

Especially preferred are compounds of formula I according to the invention, wherein $R^4$ is —$(CR^5R^6)_m$—$NR^7R^8$ and wherein m is 2, $R^5$ and $R^6$ are hydrogen and $R^7$ and $R^8$ together with the nitrogen atom to which they are attached form a heterocyclic ring selected from the group consisting of pyrrolidine, piperidine and azepane.

Preferred are further compounds of formula I according to the present invention, wherein $R^1$ is lower alkyl, with those compounds of formula I, wherein $R^1$ is isopropyl or tert-butyl, being especially preferred.

Also preferred are compounds of formula I according to the present invention, wherein $R^1$ is cycloalkyl, with those compounds of formula I, wherein $R^1$ is cyclobutyl or cyclopentyl, being especially preferred.

Thus, compounds wherein $R^1$ is selected from the group consisting of isopropyl, tert-butyl, cyclobutyl and cyclopentyl, are especially preferred. $R^2$ is preferably hydrogen or halogen. Preferably, $R^2$ is hydrogen or chloro.

More preferred are compounds of formula I according to the invention, wherein $R^2$ is hydrogen. $R^3$ is preferably hydrogen or lower alkyl. Preferably, $R^3$ is hydrogen or methyl.

More preferred are compounds of formula I according to the invention, wherein $R^3$ is hydrogen.

Preferred compounds of formula I of the present invention are the following:

(4-isopropyl-piperazin-1-yl)-[1-(1-methyl-piperidin-3-ylmethyl)-1H-indol-5-yl]-methanone,
(4-isopropyl-piperazin-1-yl)-[1-(3-morpholin-4-yl-propyl)-1H-indol-5-yl]-methanone,
(4-isopropyl-piperazin-1-yl)-[1-(1-isopropyl-pyrrolidin-3-yl)-1H-indol-5-yl]-methanone,
[1-(1-ethyl-pyrrolidin-3-yl)-1H-indol-5-yl]-(4-isopropyl-piperazin-1-yl)-methanone,
(4-cyclopentyl-piperazin-1-yl)-[1-(1-methyl-pyrrolidin-3-yl)-1H-indol-5-yl]-methanone,
(4-cyclopentyl-piperazin-1-yl)-[1-(1-ethyl-pyrrolidin-3-yl)-1H-indol-5-yl]-methanone,
[1-(1-benzyl-pyrrolidin-3-yl)-1H-indol-5-yl]-(4-cyclopentyl-piperazin-1-yl)-methanone,
(4-cyclopentyl-piperazin-1-yl)-[1-(1-isopropyl-pyrrolidin-3-yl)-1H-indol-5-yl]-methanone,
4-[5-(4-cyclopentyl-piperazine-1-carbonyl)-indol-1-yl]-1-methyl-pyrrolidin-2-one,
(4-cyclopentyl-piperazin-1-yl)-[1-(1-methyl-piperidin-3-ylmethyl)-1H-indol-5-yl]-methanone,
[1-(1-benzyl-piperidin-3-ylmethyl)-1H-indol-5-yl]-(4-cyclopentyl-piperazin-1-yl)-methanone,
(4-cyclopentyl-piperazin-1-yl)-[1-(1-ethyl-piperidin-3-ylmethyl)-1H-indol-5-yl]-methanone,
[1-(1-benzyl-pyrrolidin-3-yl)-1H-indol-5-yl]-(4-isopropyl-piperazin-1-yl)-methanone,
[1-(1-benzyl-piperidin-3-ylmethyl)-1H-indol-5-yl]-(4-isopropyl-piperazin-1-yl)-methanone,
[1-(1-ethyl-piperidin-3-ylmethyl)-1H-indol-5-yl]-(4-isopropyl-piperazin-1-yl)-methanone,
(4-cyclobutyl-piperazin-1-yl)-[1-(1-ethyl-pyrrolidin-3-yl)-1H-indol-5-yl]-methanone,
[1-(1-benzyl-pyrrolidin-3-yl)-1H-indol-5-yl]-(4-cyclobutyl-piperazin-1-yl)-methanone,
(4-cyclobutyl-piperazin-1-yl)-[1-(1-isopropyl-pyrrolidin-3-yl)-1H-indol-5-yl]-methanone,
4-[5-(4-cyclobutyl-piperazine-1-carbonyl)-indol-1-yl]-1-methyl-pyrrolidin-2-one,
(4-cyclobutyl-piperazin-1-yl)-[1-(1-methyl-piperidin-3-ylmethyl)-1H-indol-5-yl]-methanone,
[1-(1-benzyl-piperidin-3-ylmethyl)-1H-indol-5-yl]-(4-cyclobutyl-piperazin-1-yl)-methanone,
3-[5-(4-isopropyl-piperazine-1-carbonyl)-indol-1-ylmethyl]-pyrrolidine-1-carboxylic acid tert-butyl ester,
(4-isopropyl-piperazin-1-yl)-[1-((S)-1-methyl-pyrrolidin-2-ylmethyl)-1H-indol-5-yl]-methanone,
[1-((S)-1-benzyl-pyrrolidin-2-ylmethyl)-1H-indol-5-yl]-(4-isopropyl-piperazin-1-yl)-methanone,
[1-(1-benzyl-piperidin-3-yl)-1H-indol-5-yl]-(4-isopropyl-piperazin-1-yl)-methanone,
4-[5-(4-isopropyl-piperazine-1-carbonyl)-indol-1-yl]-piperidine-1-carboxylic acid tert-butyl ester,
4-[5-(4-isopropyl-piperazine-1-carbonyl)-indol-1-ylmethyl]-piperidine-1-carboxylic acid tert-butyl ester,
2-{2-[5-(4-isopropyl-piperazine-1-carbonyl)-indol-1-yl]-ethyl}-piperidine-1-carboxylic acid tert-butyl ester,
(S)-3-[5-(4-isopropyl-piperazine-1-carbonyl)-indol-1-ylmethyl]-piperidine-1-carboxylic acid tert-butyl ester,
1-(3,4-dichloro-phenyl)-4-[5-(4-isopropyl-piperazine-1-carbonyl)-indol-1-ylmethyl]-pyrrolidin-2-one,
(4-isopropyl-piperazin-1-yl)-{1-[1-(4-methoxy-phenyl)-piperidin-4-yl]-1H-indol-5-yl}-methanone,
(4-isopropyl-piperazin-1-yl)-{1-[1-(4-trifluoromethyl-phenyl)-piperidin-4-yl]-1H-indol-5-yl}-methanone,
3-[5-(4-cyclopentyl-piperazine-1-carbonyl)-indol-1-ylmethyl]-pyrrolidine-1-carboxylic acid tert-butyl ester,
[1-((S)-1-benzyl-pyrrolidin-2-ylmethyl)-1H-indol-5-yl]-(4-cyclopentyl-piperazin-1-yl)-methanone,
[1-(1-benzyl-piperidin-4-yl)-1H-indol-5-yl]-(4-cyclopentyl-piperazin-1-yl)-methanone,
4-[5-(4-cyclopentyl-piperazine-1-carbonyl)-indol-1-yl]-piperidine-1-carboxylic acid tert-butyl ester,
4-[5-(4-cyclopentyl-piperazine-1-carbonyl)-indol-1-ylmethyl]-piperidine-1-carboxylic acid tert-butyl ester,
2-[5-(4-cyclopentyl-piperazine-1-carbonyl)-indol-1-ylmethyl]-morpholine-4-carboxylic acid tert-butyl ester,
2-{2-[5-(4-cyclopentyl-piperazine-1-carbonyl)-indol-1-yl]-ethyl}-piperidine-1-carboxylic acid tert-butyl ester,
3-[5-(4-cyclopentyl-piperazine-1-carbonyl)-indol-1-ylmethyl]-piperidine-1-carboxylic acid tert-butyl ester,
(S)-3-[5-(4-cyclopentyl-piperazine-1-carbonyl)-indol-1-ylmethyl]-piperidine-1-carboxylic acid tert-butyl ester,
4-[5-(4-cyclopentyl-piperazine-1-carbonyl)-indol-1-ylmethyl]-1-(3,4-dichloro-phenyl)-pyrrolidin-2-one,
(4-cyclopentyl-piperazin-1-yl)-{1-[1-(4-methoxy-phenyl)-piperidin-4-yl]-1H-indol-5-yl}-methanone,
(R)-2-[5-(4-isopropyl-piperazine-1-carbonyl)-indol-1-ylmethyl]-pyrrolidine-1-carboxylic acid tert-butyl ester,
(S)-2-[5-(4-isopropyl-piperazine-1-carbonyl)-indol-1-ylmethyl]-pyrrolidine-1-carboxylic acid tert-butyl ester,
(4-isopropyl-piperazin-1-yl)-[1-(1-methyl-piperidin-3-yl)-1H-indol-5-yl]-methanone,
3-[5-(4-isopropyl-piperazine-1-carbonyl)-indol-1-ylmethyl]-piperidine-1-carboxylic acid tert-butyl ester,
(4-cyclopentyl-piperazin-1-yl)-{1-[2-(1-methyl-piperidin-2-yl)-ethyl]-1H-indol-5-yl}-methanone, (R)-2-[5-(4-cyclopentyl-piperazine-1-carbonyl)-indol-1-yl-methyl]-pyrrolidine-1-carboxylic acid tert-butyl ester,
(S)-2-[5-(4-cyclopentyl-piperazine-1-carbonyl)-indol-1-yl-methyl]-pyrrolidine-1-carboxylic acid tert-butyl ester,
(4-cyclopentyl-piperazin-1-yl)-[1-(1-ethyl-piperidin-3-yl)-1H-indol-5-yl]-methanone,
(4-cyclopentyl-piperazin-1-yl)-{1-[1-(4-trifluoromethyl-phenyl)-piperidin-4-yl]-1H-indol-5-yl}-methanone,
[1-(2-dimethylamino-ethyl)-1H-indol-5-yl]-(4-isopropyl-piperazin-1-yl)-methanone,
{1-[2-(ethyl-m-tolyl-amino)-ethyl]-1H-indol-5-yl}-(4-isopropyl-piperazin-1-yl)-methanone,
{1-[2-(benzyl-methyl-amino)-ethyl]-1H-indol-5-yl}-(4-isopropyl-piperazin-1-yl)-methanone,
[1-(2-azepan-1-yl-ethyl)-1H-indol-5-yl]-(4-isopropyl-piperazin-1-yl)-methanone,
[1-(3-dimethylamino-propyl)-1H-indol-5-yl]-(4-isopropyl-piperazin-1-yl)-methanone,
[1-(3-dimethylamino-2,2-dimethyl-propyl)-1H-indol-5-yl]-(4-isopropyl-piperazin-1-yl)-methanone,
(4-isopropyl-piperazin-1-yl)-{1-[3-(2-methyl-piperidin-1-yl)-propyl]-1H-indol-5-yl}-methanone,
(4-cyclopentyl-piperazin-1-yl)-[1-(2-diethylamino-ethyl)-1H-indol-5-yl]-methanone,
(4-cyclopentyl-piperazin-1-yl)-[1-(2-phenylamino-ethyl)-1H-indol-5-yl]-methanone,
(4-cyclopentyl-piperazin-1-yl)-{1-[2-(ethyl-m-tolyl-amino)-ethyl]-1H-indol-5-yl}-methanone,
{1-[2-(benzyl-methyl-amino)-ethyl]-1H-indol-5-yl}-(4-cyclopentyl-piperazin-1-yl)-methanone,
(4-cyclopentyl-piperazin-1-yl)-[1-(2-pyrrolidin-1-yl-ethyl)-1H-indol-5-yl]-methanone,
(4-cyclopentyl-piperazin-1-yl)-[1-(2-piperidin-1-yl-ethyl)-1H-indol-5-yl]-methanone,
[1-(2-azepan-1-yl-ethyl)-1H-indol-5-yl]-(4-cyclopentyl-piperazin-1-yl)-methanone,
(4-cyclopentyl-piperazin-1-yl)-[1-(2-morpholin-4-yl-ethyl)-1H-indol-5-yl]-methanone,
(4-cyclopentyl-piperazin-1-yl)-[1-(3-dimethylamino-2,2-dimethyl-propyl)-1H-indol-5-yl]-methanone,
(4-cyclopentyl-piperazin-1-yl)-[1-(3-piperidin-1-yl-propyl)-1H-indol-5-yl]-methanone,
(4-cyclopentyl-piperazin-1-yl)-{1-[3-(2-methyl-piperidin-1-yl)-propyl]-1H-indol-5-yl}-methanone,
(4-cyclopentyl-piperazin-1-yl)-{1-[2-(1-methyl-pyrrolidin-2-yl)-ethyl]-1H-indol-5-yl}-methanone,
(4-isopropyl-piperazin-1-yl)-[1-(3-piperidin-1-yl-propyl)-1H-indol-5-yl]-methanone,
(4-cyclopentyl-piperazin-1-yl)-[1-(2-dimethylamino-ethyl)-1H-indol-5-yl]-methanone,
(4-cyclopentyl-piperazin-1-yl)-[1-(2-dimethylamino-2-methyl-propyl)-1H-indol-5-yl]-methanone,
(4-cyclopentyl-piperazin-1-yl)-(1-{2-[(2-hydroxy-ethyl)-methyl-amino]-ethyl}-1H-indol-5-yl)-methanone,
[1-(2-aziridin-1-yl-ethyl)-1H-indol-5-yl]-(4-cyclopentyl-piperazin-1-yl)-methanone,
(4-tert-butyl-piperazin-1-yl)-[1-(1-methyl-piperidin-3-yl)-1H-indol-5-yl]-methanone,
(4-tert-butyl-piperazin-1-yl)-[1-(1-ethyl-piperidin-3-yl)-1H-indol-5-yl]-methanone,
(4-tert-butyl-piperazin-1-yl)-[1-(1-methyl-piperidin-3-ylmethyl)-1H-indol-5-yl]-methanone,
(4-tert-butyl-piperazin-1-yl)-[1-(1-isopropyl-pyrrolidin-3-yl)-1H-indol-5-yl]-methanone,
[1-(1-benzyl-pyrrolidin-3-yl)-1H-indol-5-yl]-(4-tert-butyl-piperazin-1-yl)-methanone,
[1-(1-ethyl-piperidin-3-yl)-2-methyl-1H-indol-5-yl]-(4-isopropyl-piperazin-1-yl)-methanone,
[3-Chloro-1-(1-methyl-piperidin-3-yl)-1H!-indol-5-yl]-(4-isopropyl-piperazin-1-yl)-methanone,
[3-Chloro-1-(1-ethyl-piperidin-3-yl)-1H!-indol-5-yl]-(4-isopropyl-piperazin-1-yl)-methanone,
(4-isopropyl-piperazin-1-yl)-[1-(1-propyl-piperidin-4-yl)-1H-indol-5-yl]-methanone,
{4-[5-(4-isopropyl-piperazine-1-carbonyl)-indol-1-yl]-piperidin-1-yl}-acetonitrile,
{1-[1-(2,2-difluoro-ethyl)-piperidin-4-yl]-1H-indol-5-yl}-(4-isopropyl-piperazin-1-yl)-methanone,
(4-isopropyl-piperazin-1-yl)-[1-(1-propyl-piperidin-3-ylmethyl)-1H-indol-5-yl]-methanone,
(4-isopropyl-piperazin-1-yl)-{1-[1-(2-methoxy-ethyl)-piperidin-3-ylmethyl]-1H-indol-5-yl}-methanone,
{(R)-3-[5-(4-isopropyl-piperazine-1-carbonyl)-indol-1-yl]-pyrrolidin-1-yl}-acetonitrile,
[1-((S)-1-ethyl-pyrrolidin-3-yl)-1H-indol-5-yl]-(4-isopropyl-piperazin-1-yl)-methanone,
{(S)-3-[5-(4-isopropyl-piperazine-1-carbonyl)-indol-1-yl]-pyrrolidin-1-yl}-acetonitrile,
[1-((S)-1-cyclopentyl-pyrrolidin-3-yl)-1H-indol-5-yl]-(4-isopropyl-piperazin-1-yl)-methanone,
(4-isopropyl-piperazin-1-yl)-[1-(1-isopropyl-piperidin-4-ylmethyl)-1H-indol-5-yl]-methanone,
and pharmaceutically acceptable salts thereof.

Especially preferred are the following compounds:
(4-isopropyl-piperazin-1-yl)-[1-(1-isopropyl-pyrrolidin-3-yl)-1H-indol-5-yl]-methanone,
(4-cyclopentyl-piperazin-1-yl)-[1-(1-ethyl-pyrrolidin-3-yl)-1H-indol-5-yl]-methanone,
(4-cyclopentyl-piperazin-1-yl)-[1-(1-isopropyl-pyrrolidin-3-yl)-1H-indol-5-yl]-methanone,
[1-(1-ethyl-piperidin-3-ylmethyl)-1H-indol-5-yl]-(4-isopropyl-piperazin-1-yl)-methanone,
(4-cyclobutyl-piperazin-1-yl)-[1-(1-ethyl-pyrrolidin-3-yl)-1H-indol-5-yl]-methanone,
(4-cyclobutyl-piperazin-1-yl)-[1-(1-isopropyl-pyrrolidin-3-yl)-1H-indol-5-yl]-methanone,
[1-(1-benzyl-piperidin-3-ylmethyl)-1H-indol-5-yl]-(4-cyclobutyl-piperazin-1-yl)-methanone,
[1-((S)-1-benzyl-pyrrolidin-2-ylmethyl)-1H-indol-5-yl]-(4-isopropyl-piperazin-1-yl)-methanone,
[1-(1-benzyl-piperidin-3-yl)-1H-indol-5-yl]-(4-isopropyl-piperazin-1-yl)-methanone,
[1-((S)-1-benzyl-pyrrolidin-2-ylmethyl)-1H-indol-5-yl]-(4-cyclopentyl-piperazin-1-yl)-methanone,
(4-isopropyl-piperazin-1-yl)-[1-(1-methyl-piperidin-3-yl)-1H-indol-5-yl]-methanone,
(4-cyclopentyl-piperazin-1-yl)-{1-[2-(1-methyl-piperidin-2-yl)-ethyl]-1H-indol-5-yl}-methanone,
[1-(2-azepan-1-yl-ethyl)-1H-indol-5-yl]-(4-isopropyl-piperazin-1-yl)-methanone,
(4-cyclopentyl-piperazin-1-yl)-[1-(2-pyrrolidin-1-yl-ethyl)-1H-indol-5-yl]-methanone,
(4-cyclopentyl-piperazin-1-yl)-[1-(2-piperidin-1-yl-ethyl)-1H-indol-5-yl]-methanone
[1-(2-azepan-1-yl-ethyl)-1H-indol-5-yl]-(4-cyclopentyl-piperazin-1-yl)-methanone,
(4-cyclopentyl-piperazin-1-yl)-[1-(2-dimethylamino-2-methyl-propyl)-1H-indol-5-yl]-methanone,

[1-(1-ethyl-piperidin-3-yl)-2-methyl-1H-indol-5-yl]-(4-isopropyl-piperazin-1-yl)-methanone,
[1-((S)-1-cyclopentyl-pyrrolidin-3-yl)-1H-indol-5-yl]-(4-isopropyl-piperazin-1-yl)-methanone,
and any pharmaceutically acceptable salt thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises:

(a) reacting a compound of formula II:

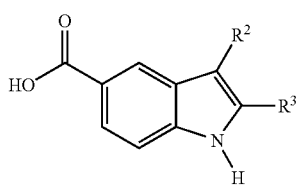

II wherein $R^2$ and $R^3$ are as defined herein before, with a piperazine of the formula III:

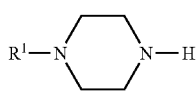

III wherein $R^1$ is as defined herein before, in the presence of a coupling reagent under basic conditions to obtain a compound of the formula IV:

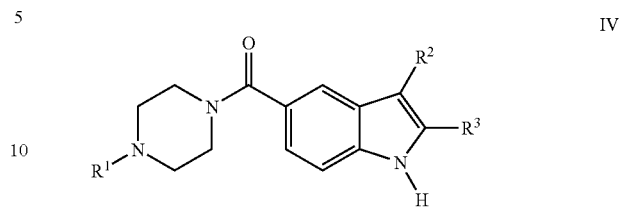

IV wherein $R^1$, $R^2$ and $R^3$ are as defined herein before, and (b) chemically converting the compound of formula IV into a compound of formula I:

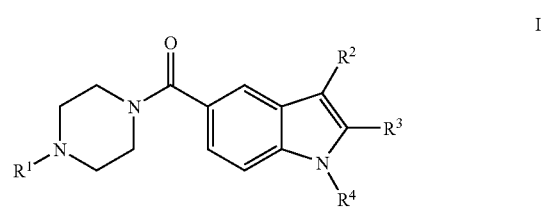

I wherein $R^4$ is a group as defined herein before, and, (c) optionally converting the compound obtained into a pharmaceutically acceptable acid addition salt.

Appropriate coupling reagents are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU). Preferably, the coupling reagent is selected from the group consisting of 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT) and O-benzotriazol-1-yl-N,N,N',N'-tetramethyluronium tetrafluoroborate (TBTU). The reaction is carried out in a suitable solvent such as for example dimethylformamide (DMF) or dioxane in the presence of an appropriate base. Preferred is a base such as triethylamine or diisopropylethylamine.

"Chemcially converting" into a compound of formula I means treating the compound of formula IV with a suitable base in a suitable solvent under anhydrous conditions (e.g. sodium hydride in DMF) and reacting the intermediate anion with an alkylating or acylating agent $R^4$—X, wherein X signifies a leaving group such as e.g. iodide, bromide, methanesulfonate or chloride, to obtain a compound of formula I; or alternatively, "chemcially converting" into a compound of formula I means reacting a compound of formula IV with an optionally substituted phenylboronic acid using an appropriate catalyst (e.g. copper(II) acetate) and base (e.g. pyridine) in a suitable solvent like, e.g. dichloromethane, to obtain compounds of formula I.

In more detail, the compounds of formula I can be manufactured by the methods given below, by the methods given in the examples or by analogous methods. The preparation of compounds of formula I of the present invention may be carried out in sequential or convergent synthetic routes. The skills required for carrying out the reaction and for purification of the resulting products are known to those skilled in the art. The substituents and indices used in the following description of the processes have the significance given herein before unless indicated to the contrary. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

There is no particular restriction on the nature of the coupling reagent used in this stage, and any coupling reagent commonly used in this type of reaction may equally be employed here. Examples of such reducing agents include N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the

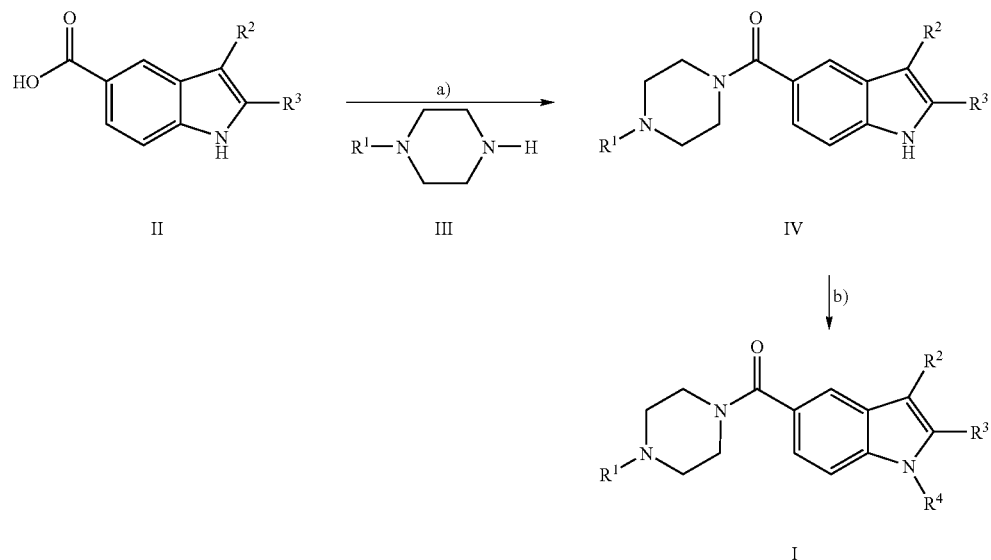

a) Indole-5-carboxylic acids II are either commercially available or can be synthesized via methods known to those in the art. (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, we find it convenient to transform indole-5-carboxylic acid derivatives II into the respective piperazine amide IV through amide coupling with substituted piperazines (either commercially available or accessible by methods described in references or by methods known in the art; as appropriate) by employing a coupling reagent. The reaction may be carried out in the presence or absence of a solvent and a base. There is no particular restriction on the nature of the solvent to be employed, provided that it has no adverse effect on the reaction or the reagents involved and that it can dissolve the reagents, at least to some extent. Examples for suitable solvents include: DMF, THF, dioxane, and the like. There is no particular restriction on the nature of the base used in this stage, and any base commonly used in this type of reaction may equally be employed here. Examples of such bases include NEt₃ or DIPEA, and the like.

reaction temperature and the nature of the reagents. However, a period of from 0.5 h to several days will usually suffice to yield compounds IV.

b) The indole nitrogen in IV can be substituted in many ways and under varying reaction conditions which are known to those in the art. However we find it convenient to either react indole derivatives IV with tosylates, mesylates, halogenides as appropriate (either commercially available or accessible by methods described in references or by methods known in the art; as appropriate). The reaction may be carried out in the presence or absence of a solvent and a base. There is no particular restriction on the nature of the solvent to be employed, provided that it has no adverse effect on the reaction or the reagents involved and that it can dissolve the reagents, at least to some extent. Examples for suitable solvents include: THF, dioxane, and the like. There is no particular restriction on the nature of the base used in this stage, and any base commonly used in this type of reaction may equally be employed here. Examples of such bases include KOtBu or NaH, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds of formula I. Complementarily to such a procedure indole derivatives IV might be reacted with suitable alcohols (either commercially available or accessible by methods described in references or by methods known in the art; as appropriate) in the presence of a coupling reagent and a solvent. There is no particular restriction on the nature of the coupling reagent used in this stage, and any coupling reagent commonly used in this type of reaction may equally be employed here. Examples of such reducing agents include cyanomethylenetri-n-butylphosphorane or cyanomethylenetrimethyl phosphorane and the like (Lit: THL 2002, 43, 2187-2190). There is no particular restriction on the nature of the solvent to be employed, provided that it has no adverse effect on the reaction or the reagents involved and that it can dissolve the reagents, at least to some extent. Examples for suitable solvents include: toluene, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds I. However, the resulting compound is a derivative of a compound of formula I that contains an N-heterocyclic ring wherein the nitrogen atom is unsubstituted (removal of a protecting group (R'=—COOR$^9$) from any nitrogen atom embodied in R$^4$ to arrive at compounds wherein R'=H). These derivatives are subjected to consecutive reactions under many possible reaction conditions. However, we find it convenient to substitute said deprotected nitrogen via alkylation or reductive amination under suitable conditions. Alkylation can be done with any suitable alkylating agent, in the presence or absence of a base and in the presence or absence of a solvent. There is no particular restriction on the nature of the solvent to be employed, provided that it has no adverse effect on the reaction or the reagents involved and that it can dissolve the reagents, at least to some extent. Examples for suitable solvents include: THF, dioxane, and the like. There is no particular restriction on the nature of the base used in this stage, and any base commonly used in this type of reaction may equally be employed here. Examples of such bases include KOtBu or NaH, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds of formula I. Reductive aminations can be carried out under acidic conditions in the presence or absence of a solvent with a reducing agent. There is no particular restriction on the nature of the solvent to be employed, provided that it has no adverse effect on the reaction or the reagents involved and that it can dissolve the reagents, at least to some extent. Examples for suitable solvents include: THF, dioxane, methanol and the like. There is no particular restriction on the nature of the acid used in this stage, and any acid commonly used in this type of reaction may equally be employed here. Examples of such acids include acetic acid, and the like. There is no particular restriction on the nature of the reducing agent used in this stage, and any reducing agent commonly used in this type of reaction may equally be employed here. Examples of such reducing agents include sodium triacetoxyborohydride, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds I.

The compounds of formula I can contain several asymmetric centers and can be present in the form of optically pure enantiomers, mixtures of enantiomers such as, e.g. racemates, optically pure diastereomers, mixtures of diastereomers, diastereomeric racemates or mixtures of diastereomeric racemates. The optically active forms can be obtained for example by resolution of the racemates, by asymmetric synthesis or asymmetric chromatography (chromatography with a chiral adsorbent or eluant).

As described above, the compounds of formula I of the present invention can be used as pharmaceutical compositions for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of pharmaceutical compositions for the treatment and/or prevention of diseases which are associated with the modulation of H3 receptors. The use of compounds of formula I as defined above for the preparation of pharmaceutical compositions for the treatment and/or prevention of obesity is preferred.

Furthermore, the present invention relates to the use of a compound of formula I for the manufacture of a pharmaceutical composition for the treatment and prevention of obesity in a patient who is also receiving treatment with a lipase inhibitor and particularly, wherein the lipase inhibitor is orlistat.

It is a further preferred object of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a pharmaceutical composition for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an object of the present invention.

The use of a compound of formula I in the manufacture of a pharmaceutical composition for the treatment and prevention of obesity in a patient who is also receiving treatment with a a lipase inhibitor, preferably with tetrahydrolipstatin, is also an object of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; and 8) α-Glucosidase inhibitors such as acarbose (precose) or miglitol (glyset), and the like.

Also an object of the invention is the method as described above for the simultaneous, separate or sequential administration of a compound according to formula I and a therapeutically effective amount of an anti-diabetic agent.

The use of a compound of formula I in the manufacture of a pharmaceutical composition for the treatment and prevention of Type II diabetes in a patient who is also receiving treatment with an anti-diabetic agent is also an object of the present invention.

It is a further preferred object to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an object of the invention is the method as described above for the simultaneous, separate or sequential administration of a compound according to formula I and a therapeutically effective amount of a lipid lowering agent.

The use of a compound of formula I in the manufacture of a pharmaceutical composition for the treatment and prevention of dyslipidemias in a patient who is also receiving treatment with a lipid lowering agent, is also an object of the present invention.

It is a further preferred object to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan, A308165, and the like.

Also an object of the invention is the method as described above for the simultaneous, separate or sequential administration of a compound according to formula I and a therapeutically effective amount of an anti-hypertensive agent.

The use of a compound of formula I in the manufacture of a pharmaceutical composition for the treatment and prevention of hypertension in a patient who is also receiving treatment with an anti-hypertensive agent, is also an object of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H—(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R) α-Methylhistamine di-hydrochloride (0.10 to 10 nM). Non specific binding was determined using a 200 fold excess of cold (R)α-methyl-histamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then scintillation fluid (Microscint 40, 40 microl in each well) was added and the amount of radioactivity on the filter was determined in Packard topcounter after shaking the plates for two hours at 200 rpm at room temperature.

Binding Buffer: 50 mM Tris-HCl pH 7.4 and 5 mM MgCl$_2$×6H$_2$O pH 7.4. Washing Buffer: 50 mM Tris-HCl pH 7.4 and 5 mM MgCl$_2$×6H$_2$O and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human H3R—CHO cell line. An appropriate amount of protein, e.g. approximately 500 cpm binding of RAMH at Kd, were incubated for 1 hour at room temperature in 250 µl final volume in 96-well plates in presence of $^3$H(R)α-methylhistamine (1 nM final concentration=Kd). Non-specific binding was determined using a 200 fold excess of cold (R)α-methylhistamine dihydrobromide.

All compounds were tested at a single concentration in duplicate. Compounds that showed an inhibition of [$^3$H]-RAMH by more than 50% were tested again to determine IC$_{50}$ in a serial dilution experiment, meaning concentrations were spanning 10 points starting from $4.6 \times 10^{-6}$ M to $1.0 \times 10^{-9}$ M. The dilution factor was 1/2.15 for the whole series. The concentration at which 50% inhibition of the radioligand $^3$H(R)α-methylhistamine is obtained (the IC$_{50}$) is determined from the linear regression of a plot of the logarithm of the concentration versus percent inhibition measured for the different concentrations. Ki's were calculated from IC$_{50}$ based on Cheng-Prusoff equation (Cheng, Y, Prusoff, W H (1973) Biochem Pharmacol 22, 3099-3108): Ki=IC50/[1+D/Kd] wherein D is the concentration of the radioligand and Kd is the binding constant for the radioligand binding to the receptor under the conditions used in the competition experiment.

The compounds of the present invention exhibit K$_i$ values within the range of about 1 nM to about 1000 nM, preferably of about 1 nM to about 100 nM, and more preferably of about 1 nM to about 30 nM, most preferably of about 1 nM to about 20 nM. The following table shows measured values for some selected compounds of the present invention.

|  | K$_i$ (nM) |
|---|---|
| Example 6 | 5.9 |
| Example 11 | 12.1 |
| Example 59 | 15.4 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAI mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAI mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

The following are a list of abbreviations and/or acronyms with their corresponding definitions used in the examples below: THF refers to tetrahydrofuran; TBTU refers to N,N,N',N'-tetramethyl-O-(benzotriazol-1-yl)uronium tetrafluoroborate; DIPEA refers to N,N'-diisopropylethylamine; DMF refers to N,N-dimethylformamide; DCM refers to dichloromethane; MeOH refers to methanol; KOtBu refers to potassium tert-butoxide; HPLC refers to high-performance liquid chromatography; MS(m/e) refers to mass spectrometry (m/e=mass over electron charge); and MH$^+$ is a term used in mass spectrometry and refers to molecular weight plus hydrogen.

EXAMPLES

Intermediate 1

(1H-Indol-5-yl)-(4-isopropyl-piperazin-1-yl)-methanone

A mixture of 3.23 g (20 mmol) indole-5-caboxylic acid (commercially available), 3.07 g (24 mmol) 1-(2-propyl)-piperazine (commercially available), 8.03 g (25 mmol) TBTU and 10.3 mL (60 mmol) DIPEA in 50 mL DMF was stirred for 2 h (hours) at room temperature. After evaporation of all volatiles the residue was extracted with ethyl acetate, the combined organic layers dried with $MgSO_4$ and evaporated to dryness. The residue was subsequently purified by flash column chromatography eluting with a mixture formed from DCM, MeOH, and $NH_3$ aq. to yield after evaporation of the combined product fractions 5.1 g (94%) of the title compound as light brown foam. MS(m/e): 272.3 ($MH^+$).

Intermediate 2

(4-Cyclobutyl-piperazin-1-yl)-(1H-indol-5-yl)-methanone

According to the procedure described for the synthesis of (1H-indol-5-yl)-(4-isopropyl-piperazin-1-yl)-methanone (intermediate 1) the title compound was prepared from indole-5-caboxylic acid (commercially available) and 1-cyclobutyl-piperazine (commercially available). MS(m/e): 284.0 ($MH^+$).

Intermediate 3

(4-Cyclopentyl-piperazin-1-yl)-(1H-indol-5-yl)-methanone

According to the procedure described for the synthesis of (1H-indol-5-yl)-(4-isopropyl-piperazin-1-yl)-methanone (intermediate 1) the title compound was prepared from indole-5-caboxylic acid (commercially available) and 1-cyclopentyl-piperazine (commercially available). MS(m/e): 298.5 ($MH^+$).

Intermediate 4

(4-tert-Butyl-piperazin-1-yl)-(1H-indol-5-yl)-methanone

According to the procedure described for the synthesis of (1H-indol-5-yl)-(4-isopropyl-piperazin-1-yl)-methanone (intermediate 1) the title compound was prepared from indole-5-caboxylic acid (commercially available) and 1-tert.-butyl-piperazine (commercially available). MS(m/e): 286.1 ($MH^+$).

Intermediate 5

(4-Isopropyl-piperazin-1-yl)-(2-methyl-1H-indol-5-yl)-methanone

According to the procedure described for the synthesis of (1H-indol-5-yl)-(4-isopropyl-piperazin-1-yl)-methanone (intermediate 1) the title compound was prepared from 2-methyl-1H-indole-5-carboxylic acid (commercially available) and 1-(2-propyl)-piperazine (commercially available). MS(m/e): 158.3 ($MH^+$-i-propyl-piperazine).

Intermediate 6

Toluene-4-sulfonic acid 1-methyl-piperidin-3-ylmethyl ester

A mixture of 2.07 g (16 mmol) 1-methyl-3-piperidinemethanol, 3.35 g (18 mmol) p-toluensulfonyl chloride, 0.58 g (5 mmol) 4-dimethylaminopyridine and 2.23 mL (16 mmol) $NEt_3$ in 30 mL DCM was stirred for 2 h at room temperature. The mixture was washed with water and evaporated to dryness to yield 4.5 g (99%) of the title compound as yellow oil which was used without further purification. MS(m/e): 284.1 ($MH^+$).

Intermediate 7

Toluene-4-sulfonic acid 1-isopropyl-pyrrolidin-3-yl ester

According to the procedure described for the synthesis of toluene-4-sulfonic acid 1-methyl-piperidin-3-ylmethyl ester (intermediate 6) the title compound was prepared from 1-isopropyl-3-pyrrolidinol (commercially available) and p-toluensulfonyl chloride (commercially available). MS(m/e): 284.0 ($MH^+$).

Intermediate 8

Toluene-4-sulfonic acid 1-ethyl-pyrrolidin-3-yl ester

According to the procedure described for the synthesis of toluene-4-sulfonic acid 1-methyl-piperidin-3-ylmethyl ester (intermediate 6) the title compound was prepared from 1-ethyl-pyrrolidin-3-ol (commercially available) and p-toluensulfonyl chloride (commercially available). MS(m/e): 270.0 ($MH^+$).

Intermediate 9

Toluene-4-sulfonic acid 1-methyl-pyrrolidin-3-yl ester

According to the procedure described for the synthesis of toluene-4-sulfonic acid 1-methyl-piperidin-3-ylmethyl ester (intermediate 6) the title compound was prepared from 1-methyl-pyrrolidin-3-ol (commercially available) and p-toluensulfonyl chloride (commercially available). MS(m/e): 256 ($MH^+$).

Intermediate 10

Toluene-4-sulfonic acid 1-benzyl-pyrrolidin-3-yl ester

According to the procedure described for the synthesis of toluene-4-sulfonic acid 1-methyl-piperidin-3-ylmethyl ester (intermediate 6) the title compound was prepared from 1-benzyl-pyrrolidin-3-ol (commercially available) and p-toluensulfonyl chloride (commercially available). MS(m/e): 332 ($MH^+$).

Intermediate 11

Toluene-4-sulfonic acid 1-methyl-5-oxo-pyrrolidin-3-yl ester

According to the procedure described for the synthesis of toluene-4-sulfonic acid 1-methyl-piperidin-3-ylmethyl ester (intermediate 6) the title compound was prepared from 4-hydroxa-1-methyl-pyrrolidin-2-one (commercially available) and p-toluensulfonyl chloride (commercially available). MS(m/e): 270 (MH$^+$).

Intermediate 12

Toluene-4-sulfonic acid 1-benzyl-piperidin-3-ylmethyl ester a) Step 1: 3-(Toluene-4-sulfonyloxymethyl)-piperidine-1-carboxylic acid tert-butyl ester According to the procedure described for the synthesis of toluene-4-sulfonic acid 1-methyl-piperidin-3-ylmethyl ester (intermediate 6) the title compound was prepared from 3-hydroxymethyl-piperidine-1-carboxylic acid tert-butyl ester (commercially available) and p-toluensulfonyl chloride (commercially available). MS(m/e): 270 (MH$^+$-Boc).

b) Step 2: Toluene-4-sulfonic acid piperidin-3-ylmethyl ester, hydrochloride

A mixture of 8.5 g (23 mmol) 3-(toluene-4-sulfonyloxymethyl)-piperidine-1-carboxylic acid tert-butyl ester and 28.7 mL (115 mmol) 4N HCl in dioxane in 30 mL dioxane was evaporated to dryness. This yielded 7.57 g (97%) of the title compound as viscous yellow oil which was used without further purification. MS(m/e): 270 (MH$^+$).

c) Step 3: Toluene-4-sulfonic acid 1-benzyl-piperidin-3-ylmethyl ester

A mixture of 1.4 g (4.6 mmol) toluene-4-sulfonic acid piperidin-3-ylmethyl ester, hydrochloride, 2.43 g (23 mmol) benzaldehyde (commercially available), 2.62 mL (46 mmol) acetic acid and 2.9 g (14 mmol) sodium triacetoxyborohydride in 25 mL THF was heated to 90° C. After evaporation of the volatiles isolute was added and subsequently purified by flash column chromatography eluting with a mixture formed from DCM, MeOH and NH$_3$ aq. to yield after evaporation of the combined product fractions 1.03 g (50%) of the title compound as light yellow oil. MS(m/e): 360 (MH$^+$).

Intermediate 13

Toluene-4-sulfonic acid 1-ethyl-piperidin-3-ylmethyl ester

A mixture of 1 g (3.2. mmol) toluene-4-sulfonic acid piperidin-3-ylmethyl ester, hydrochloride, 1.02 g (7 mmol) ethyl iodide (commercially available) and 0.6 g (10 mmol) sodium carbonate in 20 mL acetonitrile was shaken at 65° C. overnight. Sodium hydrogencarbonate aq. was added and the mixture was extracted with DCM. The combined organic fractions were evaporated to dryness and the residue was purified by preparative HPLC on reversed phase eluting with a gradient formed from acetonitrile/water/NEt3. The combined product fractions were evaporated to yield 40 mg (4%) of the title compound as yellow oil. MS(m/e): 298 (MH$^+$).

Intermediate 14

Toluene-4-sulfonic acid 3-morpholin-4-yl-propyl ester

According to the procedure described for the synthesis of toluene-4-sulfonic acid 1-methyl-piperidin-3-ylmethyl ester (intermediate 6) the title compound was prepared 2-Morpholin-4-yl-ethanol (commercially available) and p-toluensulfonyl chloride (commercially available). MS(m/e): 300.1 (MH$^+$).

Intermediate 15

(3-Chloro-1H-indol-5-yl)-(4-isopropyl-piperazin-1-yl)-methanone a) Step 1: 3-Chloro-1H-indole-5-carboxylic acid methyl ester A mixture of 1.4 g (8 mmol) 1H-indole-5-carboxylic acid methyl ester and 1.28 g (9.6 mmol) N-chlorosuccinimid in 40 mL methanol was stirred at room temperature for 16 h. The mixture was evaporated to dryness and taken up in DCM washed with 1N NaHCO$_3$ aq, dried with MgSO$_4$, filtered and evaporated to dryness to yield 1.05 g (62%) of the title compound. MS(m/e): 210.1 (MH$^+$).

b) Step 2: (3-Chloro-1H-indol-5-yl)-(4-isopropyl-piperazin-1-yl)-methanone

A mixture of 1.05 g (5 mmol) 3-Chloro-1H-indole-5-carboxylic acid methyl ester and 1.05 g (25 mmol) LiOH.H$_2$O in THF, methanol, water was stirred at 50° C. for 4 h. The mixture was evaporated to dryness and the corresponding acid was used without further purification in the subsequent step. 0.77 g (6 mmol) 1-(2-propyl)-piperazine, 2.4g (7.5 mmol) TBTU, 2.5 g (25 mmol) NEt$_3$ and 20 mL DMF was added and the mixture was stirred at room temperature for 4 h. 1N NaHCO$_3$ was added and the mixture was extracted with DCM. The combined organic layers were dried with MgSO$_4$, filtered and evaporated. The residue was purified by flash column chromatography on silica eluting with a gradient formed from heptane, ethyl acetate, methanol and NEt$_3$. The combined product fractions were evaporated to yield 0.67 g (44%) of the title compound as light brown solid. MS(m/e): 306.3 (MH$^+$).

Example 1

(4-Isopropyl-piperazin-1-yl)-[1-(1-methyl-piperidin-3-ylmethyl)-1H-indol-5-yl]-methanone A mixture of 1.06 g (3.9 mmol) (1H-indol-5-yl)-(4-isopropyl-piperazin-1-yl)-methanone (intermediate 1); 0.484 g (4.3 mmol) KOtBu and 1.33 g (4.7 mmol) toluene-4-sulfonic acid 1-methyl-piperidin-3-ylmethyl ester (intermediate 6) in 20 mL THF was shaken at 60° C. for 3 h. After evaporation of all volatiles a mixture ethyl acetate was added and washed with water. The organic phase was dried with MgSO$_4$ and evaporated to dryness. The residue was purified by column chromatography on silica eluting with a solvent mixture formed from DCM, methanol NEt$_3$. The combined product fractions were evaporated to yield 1.44 g (91%) of the title compound as light yellow gum. MS(m/e): 383.5 (MH$^+$).

In analogy to the procedure described for the synthesis of (4-isopropyl-piperazin-1-yl)-[1-(1-methyl-piperidin-3-ylmethyl)-1H-indol-5-yl]-methanone (example 1) further indole derivatives have been synthesized from their respective starting materials mentioned in table 1. The purification of the compounds can alternatively be achieved by preparative HPLC purification on reversed phase eluting with a gradient formed from acetonitrile, water, NEt$_3$. The examples are shown in table 1 and comprise example 2-example 21.

TABLE 1

| No | MW | Name | Starting materials | MH+ found |
|----|------|------|--------------------|-----------|
| 2 | 398.6 | (4-isopropyl-piperazin-1-yl)-[1-(3-morpholin-4-yl-propyl)-1H-indol-5-yl]-methanone | (1H-indol-5-yl)-(4-isopropyl-piperazin-1-yl)-methanone (intermediate 1) and toluene-4-sulfonic acid 3-morpholin-4-yl-propyl ester (intermediate 14) | 399.2 |
| 3 | 382.6 | (4-isopropyl-piperazin-1-yl)-[1-(1-isopropyl-pyrrolidin-3-yl)-1H-indol-5-yl]-methanone | (1H-indol-5-yl)-(4-isopropyl-piperazin-1-yl)-methanone (intermediate 1) and toluene-4-sulfonic acid 1-isopropyl-pyrrolidin-3-yl ester (intermediate 7) | 383.4 |
| 4 | 368.52 | [1-(1-ethyl-pyrrolidin-3-yl)-1H-indol-5-yl]-(4-isopropyl-piperazin-1-yl)-methanone | (1H-indol-5-yl)-(4-isopropyl-piperazin-1-yl)-methanone (intermediate 1) and toluene-4-sulfonic acid 1-ethyl-pyrrolidin-3-yl ester (intermediate 8) | 369.0 |
| 5 | 380.54 | (4-cyclopentyl-piperazin-1-yl)-[1-(1-methyl-pyrrolidin-3-yl)-1H-indol-5-yl]-methanone | (4-cyclopentyl-piperazin-1-yl)-(1H-indol-5-yl)-methanone (intermediate 3) and toluene-4-sulfonic acid 1-methyl-pyrrolidin-3-yl ester (intermediate 9) | 381.4 |
| 6 | 394.56 | (4-cyclopentyl-piperazin-1-yl)-[1-(1-ethyl-pyrrolidin-3-yl)-1H-indol-5-yl]-methanone | (4-cyclopentyl-piperazin-1-yl)-(1H-indol-5-yl)-methanone (intermediate 3) and toluene-4-sulfonic acid 1-ethyl-pyrrolidin-3-yl ester (intermediate 8) | 395.5 |
| 7 | 456.63 | [1-(1-benzyl-pyrrolidin-3-yl)-1H-indol-5-yl]-(4-cyclopentyl-piperazin-1-yl)-methanone | (4-cyclopentyl-piperazin-1-yl)-(1H-indol-5-yl)-methanone (intermediate 3) and toluene-4-sulfonic acid 1-benzyl-pyrrolidin-3-yl ester (intermediate 10) | 457.4 |
| 8 | 408.59 | (4-cyclopentyl-piperazin-1-yl)-[1-(1-isopropyl-pyrrolidin-3-yl)-1H-indol-5-yl]-methanone | (4-cyclopentyl-piperazin-1-yl)-(1H-indol-5-yl)-methanone (intermediate 3) and toluene-4-sulfonic acid 1-isopropyl-pyrrolidin-3-yl ester (intermediate 7) | 409.5 |
| 9 | 394.52 | 4-[5-(4-cyclopentyl-piperazine-1-carbonyl)-indol-1-yl]-1-methyl-pyrrolidin-2-one | (4-cyclopentyl-piperazin-1-yl)-(1H-indol-5-yl)-methanone (intermediate 3) and toluene-4-sulfonic acid 1-methyl-5-oxo-pyrrolidin-3-yl ester (intermediate 11) | 395.4 |
| 10 | 408.59 | (4-cyclopentyl-piperazin-1-yl)-[1-(1-methyl-piperidin-3-ylmethyl)-1H-indol-5-yl]-methanone | (4-cyclopentyl-piperazin-1-yl)-(1H-indol-5-yl)-methanone (intermediate 3) and toluene-4-sulfonic acid 1-methyl-piperidin-3-ylmethyl ester (intermediate 6) | 409.5 |
| 11 | 484.69 | [1-(1-benzyl-piperidin-3-ylmethyl)-1H-indol-5-yl]-(4-cyclopentyl-piperazin-1-yl)-methanone | (4-cyclopentyl-piperazin-1-yl)-(1H-indol-5-yl)-methanone (intermediate 3) and toluene-4-sulfonic acid 1-benzyl-piperidin-3-ylmethyl ester (intermediate 12) | 485.4 |
| 12 | 422.62 | (4-cyclopentyl-piperazin-1-yl)-[1-(1-ethyl-piperidin-3-ylmethyl)-1H-indol-5-yl]-methanone | (4-cyclopentyl-piperazin-1-yl)-(1H-indol-5-yl)-methanone (intermediate 3) and toluene-4-sulfonic acid 1-ethyl-piperidin-3-ylmethyl ester (intermediate 13) | 423.4 |
| 13 | 430.6 | [1-(1-benzyl-pyrrolidin-3-yl)-1H-indol-5-yl]-(4-isopropyl-piperazin-1-yl)-methanone | (1H-indol-5-yl)-(4-isopropyl-piperazin-1-yl)-methanone (intermediate 1) and toluene-4-sulfonic acid 1-benzyl-pyrrolidin-3-yl ester (intermediate 10) | 431.4 |
| 14 | 458.65 | [1-(1-benzyl-piperidin-3-ylmethyl)-1H-indol-5-yl]-(4-isopropyl- | (1H-indol-5-yl)-(4-isopropyl-piperazin-1-yl)-methanone (intermediate 1) and | 459.4 |

TABLE 1-continued

| No | MW | Name | Starting materials | MH+ found |
|---|---|---|---|---|
|  |  | piperazin-1-yl)-methanone | toluene-4-sulfonic acid 1-benzyl-piperidin-3-ylmethyl ester (intermediate 12) |  |
| 15 | 396.58 | [1-(1-ethyl-piperidin-3-ylmethyl)-1H-indol-5-yl]-(4-isopropyl-piperazin-1-yl)-methanone | (1H-indol-5-yl)-(4-isopropyl-piperazin-1-yl)-methanone (intermediate 1) and toluene-4-sulfonic acid 1-ethyl-piperidin-3-ylmethyl ester (intermediate 13) | 397.3 |
| 16 | 380.54 | (4-cyclobutyl-piperazin-1-yl)-[1-(1-ethyl-pyrrolidin-3-yl)-1H-indol-5-yl]-methanone | (4-cyclobutyl-piperazin-1-yl)-(1H-indol-5-yl)-methanone (intermediate 2) and toluene-4-sulfonic acid 1-ethyl-pyrrolidin-3-yl ester (intermediate 8) | 381.4 |
| 17 | 442.61 | [1-(1-benzyl-pyrrolidin-3-yl)-1H-indol-5-yl]-(4-cyclobutyl-piperazin-1-yl)-methanone | (4-cyclobutyl-piperazin-1-yl)-(1H-indol-5-yl)-methanone (intermediate 2) and toluene-4-sulfonic acid 1-benzyl-pyrrolidin-3-yl ester (intermediate 10) | 443.4 |
| 18 | 394.56 | (4-cyclobutyl-piperazin-1-yl)-[1-(1-isopropyl-pyrrolidin-3-yl)-1H-indol-5-yl]-methanone | (4-cyclobutyl-piperazin-1-yl)-(1H-indol-5-yl)-methanone (intermediate 2) and toluene-4-sulfonic acid 1-isopropyl-pyrrolidin-3-yl ester (intermediate 7) | 395.4 |
| 19 | 380.49 | 4-[5-(4-cyclobutyl-piperazine-1-carbonyl)-indol-1-yl]-1-methyl-pyrrolidin-2-one | (4-cyclobutyl-piperazin-1-yl)-(1H-indol-5-yl)-methanone (intermediate 2) and toluene-4-sulfonic acid 1-methyl-5-oxo-pyrrolidin-3-yl ester (intermediate 11) | 381.4 |
| 20 | 394.56 | (4-cyclobutyl-piperazin-1-yl)-[1-(1-methyl-piperidin-3-ylmethyl)-1H-indol-5-yl]-methanone | (4-cyclobutyl-piperazin-1-yl)-(1H-indol-5-yl)-methanone (intermediate 2) and toluene-4-sulfonic acid 1-methyl-piperidin-3-ylmethyl ester (intermediate 6) | 395.4 |
| 21 | 470.66 | [1-(1-benzyl-piperidin-3-ylmethyl)-1H-indol-5-yl]-(4-cyclobutyl-piperazin-1-yl)-methanone | (4-cyclobutyl-piperazin-1-yl)-(1H-indol-5-yl)-methanone (intermediate 2) and toluene-4-sulfonic acid 1-benzyl-piperidin-3-ylmethyl ester (intermediate 12) | 471.4 |

Example 22

3-[5-(4-Isopropyl-piperazine-1-carbonyl)-indol-1-ylmethyl]-pyrrolidine-1-carboxylic acid tert-butyl ester A mixture of 21.7 mg (0.08 mmol) (1H-indol-5-yl)-(4-isopropyl-piperazin-1-yl)-methanone (intermediate 1), 24.1 mg (0.12 mmol) 3-Hydroxymethyl-pyrrolidine-1-carboxylic acid tert-butyl ester (commercially available), 38.6 mg (0.16 mmol) cyanomethylenetri-n-butylphosphorane in 1.5 mL toluene was heated to 110° C. for an extended period of time. After evaporation the residue was purified by preparative HPLC on reversed phase eluting with a gradient formed from acetonitrile/water/NEt$_3$. The combined product fractions were evaporated to yield 14.3 mg of the title compound. MS(m/e): 455.4 (MH+).

In analogy to the procedure described for the synthesis of example 22 further indole derivatives have been prepared from their respective starting materials as mentioned in table 2. The examples are shown in table 2 and comprise examples 22-84.

TABLE 2

| No. | MW | name | starting materials | MH+ found |
|---|---|---|---|---|
| 23 | 368.52 | (4-isopropyl-piperazin-1-yl)-[1-((S)-1-methyl-pyrrolidin-2-ylmethyl)-1H-indol-5-yl]-methanone | (1H-indol-5-yl)-(4-isopropyl-piperazin-1-yl)-methanone (intermediate 1) and ((S)-1-ethyl-pyrrolidin-2-yl)-methano (commercially available) | 369.4 |
| 24 | 444.62 | [1-((S)-1-benzyl-pyrrolidin-2-ylmethyl)-1H-indol-5-yl]-(4- | (1H-indol-5-yl)-(4-isopropyl-piperazin-1-yl)-methanone (intermediate 1) and ((S)-1- | 445.4 |

TABLE 2-continued

| No. | MW | name | starting materials | MH+ found |
|---|---|---|---|---|
| | | isopropyl-piperazin-1-yl)-methanone | benzyl-pyrrolidin-2-yl)-methanol (commercially available) | |
| 25 | 444.62 | [1-(1-benzyl-piperidin-3-yl)-1H-indol-5-yl]-(4-isopropyl-piperazin-1-yl)-methanone | (1H-indol-5-yl)-(4-isopropyl-piperazin-1-yl)-methanone (intermediate 1) and 1-benzyl-piperidin-3-ol (commercially available) | 445.4 |
| 26 | 454.61 | 4-[5-(4-isopropyl-piperazine-1-carbonyl)-indol-1-yl]-piperidine-1-carboxylic acid tert-butyl ester | (1H-indol-5-yl)-(4-isopropyl-piperazin-1-yl)-methanone (intermediate 1) and 4-hydroxy-piperidine-1-carboxylic acid tert-butyl ester (commercially available) | 455.4 |
| 27 | 468.64 | 4-[5-(4-isopropyl-piperazine-1-carbonyl)-indol-1-ylmethyl]-piperidine-1-carboxylic acid tert-butyl ester | (1H-indol-5-yl)-(4-isopropyl-piperazin-1-yl)-methanone (intermediate 1) and 4-hydroxymethyl-piperidine-1-carboxylic acid tert-butyl ester(commercially available) | 469.4 |
| 28 | 482.67 | 2-{2-[5-(4-isopropyl-piperazine-1-carbonyl)-indol-1-yl]-ethyl}-piperidine-1-carboxylic acid tert-butyl ester | (1H-indol-5-yl)-(4-isopropyl-piperazin-1-yl)-methanone (intermediate 1) and 2-(2-hydroxy-ethyl)-piperidine-1-carboxylic acid tert-butyl ester (commercially available) | 483.3 |
| 29 | 468.64 | (S)-3-[5-(4-isopropyl-piperazine-1-carbonyl)-indol-1-ylmethyl]-piperidine-1-carboxylic acid tert-butyl ester | (1H-indol-5-yl)-(4-isopropyl-piperazin-1-yl)-methanone (intermediate 1) and (S)-3-hydroxymethyl-piperidine-1-carboxylic acid tert-butyl ester (commercially available) | 469.4 |
| 30 | 513.47 | 1-(3,4-dichloro-phenyl)-4-[5-(4-isopropyl-piperazine-1-carbonyl)-indol-1-ylmethyl]-pyrrolidin-2-one | (1H-indol-5-yl)-(4-isopropyl-piperazin-1-yl)-methanone (intermediate 1) and 1-(3,4-dichloro-phenyl)-4-hydroxymethyl-pyrrolidin-2-one (commercially available) | 513.3 |
| 31 | 460.62 | (4-isopropyl-piperazin-1-yl)-{1-[1-(4-methoxy-phenyl)-piperidin-4-yl]-1H-indol-5-yl}-methanone | (1H-indol-5-yl)-(4-isopropyl-piperazin-1-yl)-methanone (intermediate 1) and 1-(4-methoxy-phenyl)-piperidin-4-ol (as prepared in WO 2004/033463) | 461.4 |
| 32 | 498.59 | (4-isopropy-piperazin-1-yl)-{1-[1-(4-trifluoromethyl-phenyl)-piperidin-4-yl]-1H-indol-5-yl}-methanone | (1H-indol-5-yl)-(4-isopropyl-piperazin-1-yl)-methanone (intermediate 1) and 1-(4-trifluoromethyl-phenyl)-piperidin-4-ol (as prepared in WO 2004/033463) | 499.3 |
| 33 | 480.65 | 3-[5-(4-cyclopentyl-piperazine-1-carbonyl)-indol-1-ylmethyl]-pyrrolidine-1-carboxylic acid tert-butyl ester | (4-cyclopentyl-piperazin-1-yl)-(1H-indol-5-yl)-methanone (intermediate 3) and 3-hydroxymethyl-pyrrolidine-1-carboxylic acid tert-butyl ester (commercially available) | 481.4 |
| 34 | 470.66 | [1-((S)-1-benzyl-pyrrolidin-2-ylmethyl)-1H-indol-5-yl]-(4-cyclopentyl-piperazin-1-yl)-methanone | (4-cyclopentyl-piperazin-1-yl)-(1H-indol-5-yl)-methanone (intermediate 3) and ((S)-1-benzyl-pyrrolidin-2-yl)-methanol (commercially available) | 471.4 |
| 35 | 470.66 | [1-(1-benzyl-piperidin-4-yl)-1H-indol-5-yl]-(4-cyclopentyl-piperazin-1-yl)-methanone | (4-cyclopentyl-piperazin-1-yl)-(1H-indol-5-yl)-methanone (intermediate 3) and 1-benzyl-piperidin-4-ol (commercially available) | 471.4 |
| 36 | 480.65 | 4-[5-(4-cyclopentyl-piperazine-1-carbonyl)-indol-1-yl]-piperidine-1-carboxylic acid tert-butyl ester | (4-cyclopentyl-piperazin-1-yl)-(1H-indol-5-yl)-methanone (intermediate 3) and 4-hydroxy-piperidine-1-carboxylic acid tert-butyl ester (commercially available) | 481.4 |
| 37 | 494.68 | 4-[5-(4-cyclopentyl-piperazine-1-carbonyl)-indol-1-ylmethyl]- | (4-cyclopentyl-piperazin-1-yl)-(1H-indol-5-yl)-methanone (intermediate 3) and | 495.4 |

TABLE 2-continued

| No. | MW | name | starting materials | MH+ found |
|---|---|---|---|---|
| | | piperidine-1-carboxylic acid tert-butyl ester | 4-hydroxymethyl-piperidine-1-carboxylic acid tert-butyl ester (commercially available) | |
| 38 | 496.65 | 2-[5-(4-cyclopentyl-piperazine-1-carbonyl)-indol-1-ylmethyl]-morpholine-4-carboxylic acid tert-butyl ester | (4-cyclopentyl-piperazin-1-yl)-(1H-indol-5-yl)-methanone (intermediate 3) and 2-hydroxymethyl-morpholine-4-carboxylic acid tert-butyl ester (commercially available) | 497.4 |
| 39 | 508.71 | 2-{2-[5-(4-cyclopentyl-piperazine-1-carbonyl)-indol-1-yl]-ethyl}-piperidine-1-carboxylic acid tert-butyl ester | (4-cyclopentyl-piperazin-1-yl)-(1H-indol-5-yl)-methanone (intermediate 3) and 2-(2-hydroxy-ethyl)-piperidine-1-carboxylic acid tert-butyl ester (commercially available) | 509.5 |
| 40 | 494.68 | 3-[5-(4-cyclopentyl-piperazine-1-carbonyl)-indol-1-ylmethyl]-piperidine-1-carboxylic acid tert-butyl ester | (4-cyclopentyl-piperazin-1-yl)-(1H-indol-5-yl)-methanone (intermediate 3) and 3-hydroxymethyl-piperidine-1-carboxylic acid tert-butyl ester (commercially available) | 495.4 |
| 41 | 494.68 | (S)-3-[5-(4-cyclopentyl-piperazine-1-carbonyl)-indol-1-ylmethyl]-piperidine-1-carboxylic acid tert-butyl ester | (4-cyclopentyl-piperazin-1-yl)-(1H-indol-5-yl)-methanone (intermediate 3) and 3-(S)-hydroxymethyl-piperidine-1-carboxylic acid tert-butyl ester (commercially available) | 495.5 |
| 42 | 539.51 | 4-[5-(4-cyclopentyl-piperazine-1-carbonyl)-indol-1-ylmethyl]-1-(3,4-dichloro-phenyl)-pyrrolidin-2-one | (4-cyclopentyl-piperazin-1-yl)-(1H-indol-5-yl)-methanone (intermediate 3) and 1-(3,4-dichloro-phenyl)-4-hydroxymethyl-pyrrolidin-2-one (commercially available) | 539.3 |
| 43 | 486.66 | (4-cyclopentyl-piperazin-1-yl)-{1-[1-(4-methoxy-phenyl)-piperidin-4-yl]-1H-indol-5-yl}-methanone | (4-cyclopentyl-piperazin-1-yl)-(1H-indol-5-yl)-methanone (intermediate 3) and 1-(4-methoxy-phenyl)-piperidin-4-ol (as prepared in WO 2004/033463) | 487.4 |
| 44 | 454.61 | (R)-2-[5-(4-isopropyl-piperazine-1-carbonyl)-indol-1-ylmethyl]-pyrrolidine-1-carboxylic acid tert-butyl ester | (1H-indol-5-yl)-(4-isopropyl-piperazin-1-yl)-methanone (intermediate 1) and (R)-2-hydroxymethyl-pyrrolidine-1-carboxylic acid tert-butyl ester (commercially available) | 455.3 |
| 45 | 454.61 | (S)-2-[5-(4-isopropyl-piperazine-1-carbonyl)-indol-1-ylmethyl]-pyrrolidine-1-carboxylic acid tert-butyl ester | (1H-indol-5-yl)-(4-isopropyl-piperazin-1-yl)-methanone (intermediate 1) and (S)-2-hydroxymethyl-pyrrolidine-1-carboxylic acid tert-butyl ester (commercially available) | 455.4 |
| 46 | 368.52 | (4-isopropyl-piperazin-1-yl)-[1-(1-methyl-piperidin-3-yl)-1H-indol-5-yl]-methanone | (1H-indol-5-yl)-(4-isopropyl-piperazin-1-yl)-methanone (intermediate 1) and 1-methyl-piperidin-3-ol (commercially available) | 369.4 |
| 47 | 468.64 | 3-[5-(4-isopropyl-piperazine-1-carbonyl)-indol-1-ylmethyl]-piperidine-1-carboxylic acid tert-butyl ester | (1H-indol-5-yl)-(4-isopropyl-piperazin-1-yl)-methanone (intermediate 1) and 3-hydroxymethyl-piperidine-1-carboxylic acid tert-butyl ester (commercially available) | 469.4 |
| 48 | 422.62 | (4-cyclopentyl-piperazin-1-yl)-{1-[2-(1-methyl-piperidin-2-yl)-ethyl]-1H-indol-5-yl}-methanone | (4-cyclopentyl-piperazin-1-yl)-(1H-indol-5-yl)-methanone (intermediate 3) and 2-(1-methyl-piperidin-2-yl)-ethanol (commercially available) | 423.3 |
| 49 | 480.65 | (R)-2-[5-(4-cyclopentyl-piperazine-1-carbonyl)-indol-1-ylmethyl]-pyrrolidine-1-carboxylic acid tert-butyl ester | (4-cyclopentyl-piperazin-1-yl)-(1H-indol-5-yl)-methanone (intermediate 3) and (R)-2-hydroxymethyl-pyrrolidine-1-carboxylic acid tert-butyl ester (commercially available) | 481.4 |
| 50 | 480.65 | (S)-2-[5-(4-cyclopentyl-piperazine-1-carbonyl)-indol-1-ylmethyl]- | (4-cyclopentyl-piperazin-1-yl)-(1H-indol-5-yl)-methanone (intermediate 3) and | 481.4 |

TABLE 2-continued

| No. | MW | name | starting materials | MH+ found |
|---|---|---|---|---|
| | | pyrrolidine-1-carboxylic acid tert-butyl ester | (S)-2-hydroxymethyl-pyrrolidine-1-carboxylic acid tert-butyl ester (commercially available) | |
| 51 | 408.59 | (4-cyclopentyl-piperazin-1-yl)-[1-(1-ethyl-piperidin-3-yl)-1H-indol-5-yl]-methanone | (4-cyclopentyl-piperazin-1-yl)-(1H-indol-5-yl)-methanone (intermediate 3) and 1-ethyl-piperidin-3-ol (commercially available) | 409.5 |
| 52 | 524.63 | (4-cyclopentyl-piperazin-1-yl)-{1-[1-(4-trifluoromethyl-phenyl)-piperidin-4-yl]-1H-indol-5-yl}-methanone | (4-cyclopentyl-piperazin-1-yl)-(1H-indol-5-yl)-methanone (intermediate 3) and 1-(4-trifluoromethyl-phenyl)-piperidin-4-ol (WO 2004/033463) | 525.3 |
| 53 | 342.49 | [1-(2-dimethylamino-ethyl)-1H-indol-5-yl]-(4-isopropyl-piperazin-1-yl)-methanone | (1H-indol-5-yl)-(4-isopropyl-piperazin-1-yl)-methanone (intermediate 1) and 2-dimethylamino-ethanol (commercially available) | 343.4 |
| 54 | 432.61 | {1-[2-(ethyl-m-tolyl-amino)-ethyl]-1H-indol-5-yl}-(4-isopropyl-piperazin-1-yl)-methanone | (1H-indol-5-yl)-(4-isopropyl-piperazin-1-yl)-methanone (intermediate 1) and 2-(ethyl-m-tolyl-amino)-ethanol (commercially available) | 433.3 |
| 55 | 418.58 | {1-[2-(benzyl-methyl-amino)-ethyl]-1H-indol-5-yl}-(4-isopropyl-piperazin-1-yl)-methanone | (1H-indol-5-yl)-(4-isopropyl-piperazin-1-yl)-methanone (intermediate 1) and 2-(benzyl-methyl-amino)-ethanol (commercially available) | 419.3 |
| 56 | 396.58 | [1-(2-azepan-1-yl-ethyl)-1H-indol-5-yl]-(4-isopropyl-piperazin-1-yl)-methanone | (1H-indol-5-yl)-(4-isopropyl-piperazin-1-yl)-methanone (intermediate 1) and 2-azepan-1-yl-ethanol (commercially available) | 397.3 |
| 57 | 356.51 | [1-(3-dimethylamino-propyl)-1H-indol-5-yl]-(4-isopropyl-piperazin-1-yl)-methanone | (1H-indol-5-yl)-(4-isopropyl-piperazin-1-yl)-methanone (intermediate 1) and N,N'-dimethyl-propane-1,3-diamine (commercially available) | 357.3 |
| 58 | 384.57 | [1-(3-dimethylamino-2,2-dimethyl-propyl)-1H-indol-5-yl]-(4-isopropyl-piperazin-1-yl)-methanone | (1H-indol-5-yl)-(4-isopropyl-piperazin-1-yl)-methanone (intermediate 1) and 2,2,N,N-tetramethyl-propane-1,3-diamine (commercially available) | 385.5 |
| 59 | 410.61 | (4-isopropyl-piperazin-1-yl)-{1-[3-(2-methyl-piperidin-1-yl)-propyl]-1H-indol-5-yl}-methanone | (1H-indol-5-yl)-(4-isopropyl-piperazin-1-yl)-methanone (intermediate 1) and 3-(2-methyl-piperidin-1-yl)-propylamine (commercially available) | 411.5 |
| 60 | 396.58 | (4-cyclopentyl-piperazin-1-yl)-[1-(2-diethylamino-ethyl)-1H-indol-5-yl]-methanone | (4-cyclopentyl-piperazin-1-yl)-(1H-indol-5-yl)-methanone (intermediate 3) and N,N-diethyl-ethane-1,2-diamine (commercially available) | 397.3 |
| 61 | 416.57 | (4-cyclopentyl-piperazin-1-yl)-[1-(2-phenylamino-ethyl)-1H-indol-5-yl]-methanone | (4-cyclopentyl-piperazin-1-yl)-(1H-indol-5-yl)-methanone (intermediate 3) and N-phenyl-ethane-1,2-diamine (commercially available) | 417.4 |
| 62 | 458.65 | (4-cyclopentyl-piperazin-1-yl)-{1-[2-(ethyl-m-tolyl-amino)-ethyl]-1H-indol-5-yl}-methanone | (4-cyclopentyl-piperazin-1-yl)-(1H-indol-5-yl)-methanone (intermediate 3) and 2-(ethyl-m-tolyl-amino)-ethanol (commercially available) | 459.4 |
| 63 | 444.62 | {1-[2-(benzyl-methyl-amino)-ethyl]-1H-indol-5-yl}-(4-cyclopentyl-piperazin-1-yl)-methanone | (4-cyclopentyl-piperazin-1-yl)-(1H-indol-5-yl)-methanone (intermediate 3) and 2-(benzyl-methyl-amino)-ethanol (commercially available) | 445.4 |
| 64 | 394.56 | (4-cyclopentyl-piperazin-1-yl)-[1-(2-pyrrolidin-1-yl-ethyl)-1H-indol-5-yl]-methanone | (4-cyclopentyl-piperazin-1-yl)-(1H-indol-5-yl)-methanone (intermediate 3) and 2-pyrrolidin-1-yl-ethylamine (commercially available) | 395.4 |
| 65 | 408.59 | (4-cyclopentyl-piperazin-1-yl)-[1-(2-piperidin-1- | (4-cyclopentyl-piperazin-1-yl)-(1H-indol-5-yl)-methanone | 409.4 |

TABLE 2-continued

| No. | MW | name | starting materials | MH+ found |
|---|---|---|---|---|
| | | yl-ethyl)-1H-indol-5-yl]-methanone | (intermediate 3) and 2-piperidin-1-yl-ethylamine (commercially available) | |
| 66 | 422.62 | [1-(2-azepan-1-yl-ethyl)-1H-indol-5-yl]-(4-cyclopentyl-piperazin-1-yl)-methanone | (4-cyclopentyl-piperazin-1-yl)-(1H-indol-5-yl)-methanone (intermediate 3) and 2-azepan-1-yl-ethanol (commercially available) | 423.4 |
| 67 | 410.56 | (4-cyclopentyl-piperazin-1-yl)-[1-(2-morpholin-4-yl-ethyl)-1H-indol-5-yl]-methanone | (4-cyclopentyl-piperazin-1-yl)-(1H-indol-5-yl)-methanone (intermediate 3) and 2-morpholin-1-yl-ethanol (commercially available) | 411.5 |
| 68 | 410.61 | (4-cyclopentyl-piperazin-1-yl)-[1-(3-dimethylamino-2,2-dimethyl-propyl)-1H-indol-5-yl]-methanone | (4-cyclopentyl-piperazin-1-yl)-(1H-indol-5-yl)-methanone (intermediate 3) and 2,2,N,N-tetramethyl-propane-1,3-diamine (commercially available) | 411.5 |
| 69 | 422.62 | (4-cyclopentyl-piperazin-1-yl)-[1-(3-piperidin-1-yl-propyl)-1H-indol-5-yl]-methanone | (4-cyclopentyl-piperazin-1-yl)-(1H-indol-5-yl)-methanone (intermediate 3) and 3-piperidin-1-yl-propylamine (commercially available) | 423.4 |
| 70 | 436.64 | (4-cyclopentyl-piperazin-1-yl)-{1-[3-(2-methyl-piperidin-1-yl)-propyl]-1H-indol-5-yl}-methanone | (4-cyclopentyl-piperazin-1-yl)-(1H-indol-5-yl)-methanone (intermediate 3) and 3-(2-methyl-piperidin-1-yl)-propylamine (commercially available) | 437.4 |
| 71 | 408.59 | (4-cyclopentyl-piperazin-1-yl)-{1-[2-(1-methyl-pyrrolidin-2-yl)-ethyl]-1H-indol-5-yl}-methanone | (4-cyclopentyl-piperazin-1-yl)-(1H-indol-5-yl)-methanone (intermediate 3) and 2-(1-methyl-pyrrolidin-2-yl)-ethanol (commercially available) | 409.4 |
| 72 | 396.58 | (4-isopropyl-piperazin-1-yl)-[1-(3-piperidin-1-yl-propyl)-1H-indol-5-yl]-methanone | (1H-indol-5-yl)-(4-isopropyl-piperazin-1-yl)-methanone (intermediate 1) and 3-piperidin-1-yl-propylamine (commercially available) | 397.4 |
| 73 | 368.52 | (4-cyclopentyl-piperazin-1-yl)-[1-(2-dimethylamino-ethyl)-1H-indol-5-yl]-methanone | (4-cyclopentyl-piperazin-1-yl)-(1H-indol-5-yl)-methanone (intermediate 3) and 2-dimethylamino-ethanol (commercially available) | 369.4 |
| 74 | 396.58 | (4-cyclopentyl-piperazin-1-yl)-[1-(2-dimethylamino-2-methyl-propyl)-1H-indol-5-yl]-methanone | (4-cyclopentyl-piperazin-1-yl)-(1H-indol-5-yl)-methanone (intermediate 3) and 2,2,N,N-tetramethyl-propane-1,3-diamine (commercially available) | 397.3 |
| 75 | 398.55 | (4-cyclopentyl-piperazin-1-yl)-(1-{2-[(2-hydroxy-ethyl)-methyl-amino]-ethyl}-1H-indol-5-yl)-methanone | (4-cyclopentyl-piperazin-1-yl)-(1H-indol-5-yl)-methanone (intermediate 3) and 2-[(2-hydroxy-ethyl)-methyl-amino]-ethanol (commercially available) | 399.4 |
| 76 | 366.51 | [1-(2-aziridin-1-yl-ethyl)-1H-indol-5-yl]-(4-cyclopentyl-piperazin-1-yl)-methanone | (4-cyclopentyl-piperazin-1-yl)-(1H-indol-5-yl)-methanone (intermediate 3) and 2-aziridin-1-yl-ethanol (commercially available) | 367.3 |
| 77 | 382.6 | (4-tert-butyl-piperazin-1-yl)-[1-(1-methyl-piperidin-3-yl)-1H-indol-5-yl]-methanone | (4-tert-butyl-piperazin-1-yl)-(1H-indol-5-yl)-methanone (intermediate 4) and 1-methyl-piperidin-3-ol (commercially available) | 383.3 |
| 78 | 396.6 | (4-tert-butyl-piperazin-1-yl)-[1-(1-ethyl-piperidin-3-yl)-1H-indol-5-yl]-methanone | (4-tert-butyl-piperazin-1-yl)-(1H-indol-5-yl)-methanone (intermediate 4) and 1-ethyl-piperidin-3-ol (commercially available) | 397.3 |
| 79 | 396.6 | (4-tert-butyl-piperazin-1-yl)-[1-(1-methyl-piperidin-3-ylmethyl)-1H-indol-5-yl]-methanone | (4-tert-butyl-piperazin-1-yl)-(1H-indol-5-yl)-methanone (intermediate 4) and (1-methyl-piperidin-3-yl)-methanol (commercially available) | 397.3 |

TABLE 2-continued

| No. | MW | name | starting materials | MH+ found |
|---|---|---|---|---|
| 80 | 396.6 | (4-tert-butyl-piperazin-1-yl)-[1-(1-isopropyl-pyrrolidin-3-yl)-1H-indol-5-yl]-methanone | (4-tert-butyl-piperazin-1-yl)-(1H-indol-5-yl)-methanone (intermediate 4) and 1-isopropyl-pyrrolidin-3-ol (commercially available) | 397.3 |
| 81 | 444.6 | [1-(1-benzyl-pyrrolidin-3-yl)-1H-indol-5-yl]-(4-tert-butyl-piperazin-1-yl)-methanone | (4-tert-butyl-piperazin-1-yl)-(1H-indol-5-yl)-methanone (intermediate 4) and 1-benzyl-pyrrolidin-3-ol (commercially available) | 445.4 |
| 82 | 396.6 | [1-(1-ethyl-piperidin-3-yl)-2-methyl-1H-indol-5-yl]-(4-isopropyl-piperazin-1-yl)-methanone | (4-Isopropyl-piperazin-1-yl)-(2-methyl-1H-indol-5-yl)-methanone (intermediate 5) and 1-ethyl-piperidin-3-ol (commercially available) | 397.4 |
| 83 | 403 | [3-chloro-1-(1-methyl-piperidin-3-yl)-1H-indol-5-yl]-(4-isopropyl-piperazin-1-yl)-methanone | (3-chloro-1H-indol-5-yl)-(4-isopropyl-piperazin-1-yl)-methanone (intermediate 15) and 1-methyl-piperidin-3-ol (commercially available) | 403.4 |
| 84 | 417 | [3-chloro-1-(1-ethyl-piperidin-3-yl)-1H-indol-5-yl]-(4-isopropyl-piperazin-1-yl)-methanone | (3-chloro-1H-indol-5-yl)-(4-isopropyl-piperazin-1-yl)-methanone (intermediate 15) and 1-ethyl-piperidin-3-ol (commercially available) | 417.3 |

Example 85

(4-Isopropyl-piperazin-1-yl)-[1-(1-propyl-piperidin-4-yl)-1H-indol-5-yl]-methanone 4-[5-(4-isopropyl-piperazine-1-carbonyl)-indol-1-yl]-piperidine-1-carboxylic acid tert-butyl ester (example 26) was treated with 4N HCl in dioxane and evaporated to dryness. The residue was used in the consecutive step without further purification. The residue was dissolved in THF and treated with KOtBu. Propyliodide was added and heated to 60° C. After evaporation to dryness the residue was dissolved in methanol/DMF and subjected to purification by preparative HPLC on reversed phase eluting with a gradient formed from acetonitrile/water/NEt₃. The combined product fractions were evaporated to the title compound. MS (m/e): 397.3 (MH⁺).

Example 86

{4-[5-(4-isopropyl-piperazine-1-carbonyl)-indol-1-yl]-piperidin-1-yl}-acetonitrile In analogy to the procedure described for the synthesis of example 83 the title compound was prepared from 4-[5-(4-isopropyl-piperazine-1-carbonyl)-indol-1-yl]-piperidine-1-carboxylic acid tert-butyl ester (example 26) and iodoacetonitrile (commercially available) as starting materials. MS (m/e): 394.3 (MH⁺).

Example 87

{1-[1-(2,2-difluoro-ethyl)-piperidin-4-yl]-1H-indol-5-yl}-(4-isopropyl-piperazin-1-yl)-methanone In analogy to the procedure described for the synthesis of example 83 the title compound was prepared from 4-[5-(4-isopropyl-piperazine-1-carbonyl)-indol-1-yl]-piperidine-1-carboxylic acid tert-butyl ester (example 26) and 2-bromo-1,1-difluoroethane (commercially available) as starting materials. MS (m/e): 419.3 (MH⁺).

Example 88

(4-isopropyl-piperazin-1-yl)-[1-(1-propyl-piperidin-3-ylmethyl)-1H-indol-5-yl]-methanone In analogy to the procedure described for the synthesis of example 83 the title compound was prepared from 3-[5-(4-isopropyl-piperazine-1-carbonyl)-indol-1-ylmethyl]-piperidine-1-carboxylic acid tert-butyl ester (example 47) and propyliodide (commercially available) as starting materials. MS (m/e): 411.5 (MH⁺).

Example 89

(4-isopropyl-piperazin-1-yl)-{1-[1-(2-methoxy-ethyl)-piperidin-3-ylmethyl]-1H-indol-5-yl}-methanone In analogy to the procedure described for the synthesis of example 83 the title compound was prepared from 3-[5-(4-isopropyl-piperazine-1-carbonyl)-indol-1-ylmethyl]-piperidine-1-carboxylic acid tert-butyl ester (example 47) and 2-bromoethyl methyl ether (commercially available) as starting materials. MS (m/e): 427.3 (MH⁺).

Example 90

{(R)-3-[5-(4-isopropyl-piperazine-1-carbonyl)-indol-1-yl]-pyrrolidin-1-yl}-acetonitrile In analogy to the procedures described for the synthesis of example 22 and 83 the title compound was prepared from (1H-indol-5-yl)-(4-isopropyl-piperazin-1-yl)-methanone (intermediate 1), (S)-3-hydroxy-pyrrolidine-1-carboxylic acid tert-butyl ester (commercially available) and iodoacetonitrile (commercially available) as starting materials. MS (m/e): 380.4 (MH⁺).

Example 91

[1-((S)-1-ethyl-pyrrolidin-3-yl)-1H-indol-5-yl]-(4-isopropyl-piperazin-1-yl)-methanone In analogy to the procedures described for the synthesis of example 22 and 83 the title compound was prepared from (1H-indol-5-yl)-(4-isopropyl-piperazin-1-yl)-methanone (intermediate 1), (R)-3-hydroxy-pyrrolidine-1-carboxylic acid tert-butyl ester (commercially available) and ethyliodide (commercially available) as starting materials. MS (m/e): 369.4 (MH$^+$).

Example 92

{(S)-3-[5-(4-isopropyl-piperazine-1-carbonyl)-indol-1-yl]-pyrrolidin-1-yl}-acetonitrile In analogy to the procedures described for the synthesis of example 22 and 83 the title compound was prepared from (1H-indol-5-yl)-(4-isopropyl-piperazin-1-yl)-methanone (intermediate 1), (R)-3-hydroxy-pyrrolidine-1-carboxylic acid tert-butyl ester (commercially available) and iodoacetonitrile (commercially available) as starting materials. MS (m/e): 380.4 (MH$^+$).

Example 93

[1-((S)-1-cyclopentyl-pyrrolidin-3-yl)-1H-indol-5-yl]-(4-isopropyl-piperazin-1-yl)-methanone The title compound was synthesized from (S)-3-[5-(4-Isopropyl-piperazine-1-carbonyl)-indol-1-yl]-pyrrolidine-1-carboxylic acid tert-butyl ester (accessible in analogy to the procedure described for the synthesis of example 22 from (1H-indol-5-yl)-(4-isopropyl-piperazin-1-yl)-methanone (intermediate 1) and (R)-3-hydroxy-pyrrolidine-1-carboxylic acid tert-butyl ester (commercially available)) subsequent cleavage of the protecting group and standard reductive amination with cyclopentanone (commercially available) and sodium triacetoxyborohydride and purification of the reaction mixture with preparative HPLC on reversed phase eluting with a gradient formed from acetonitrile, water and NEt$_3$. MS (m/e): 409.4 (MH$^+$).

Example 94

(4-isopropyl-piperazin-1-yl)-[1-(1-isopropyl-piperidin-4-ylmethyl)-1H-indol-5-yl]-methanone In analogy to the procedure described for the synthesis of example 91 the title compound was prepared from 3-[5-(4-isopropyl-piperazine-1-carbonyl)-indol-1-ylmethyl]-piperidine-1-carboxylic acid tert-butyl ester (example 47) and acetone (commercially available) as starting materials. MS (m/e): 411.5 (MH$^+$).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |

-continued

| Gelatin capsule | |
|---|---|
| Gelatin | 75.0 mg |
| Glycerol 85% | 32.0 mg |
| Karion 83 (sorbitol) | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:

1. A compound of formula I:

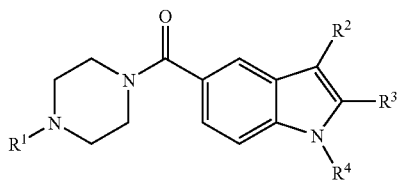

or a pharmaceutically acceptable salt thereof, wherein:
$R^1$ is lower alkyl or cycloalkyl;
$R^2$ is hydrogen or halogen;
$R^3$ is hydrogen or lower alkyl; and
$R^4$ is —$(CR^5R^6)_m$—$NR^7R^8$ or —$(CR^9R^{10})_n$-heterocyclyl, wherein:
(a) $R^5$ is hydrogen or lower alkyl;
(b) $R^6$ is hydrogen or lower alkyl;
(c) $R^7$ and $R^8$ independently from each other are selected from the group consisting of:
 (1) lower alkyl,
 (2) phenyl optionally substituted by lower alkyl,
 (3) lower phenylalkyl, and
 (4) lower hydroxyalkyl; or alternatively
$R^7$ and $R^8$ together with the nitrogen atom to which they are attached form a 3-, 4-, 5-, 6- or 7-membered saturated heterocyclic ring optionally containing a further heteroatom of oxygen or sulfur, said heterocyclic ring being optionally substituted by lower alkyl;
(d) $R^9$ is hydrogen or lower alkyl;
(e) $R^{10}$ is hydrogen or lower alkyl;
(f) said heterocyclyl of the —$(CR^9R^{10})_n$-heterocyclyl is a N-heterocyclic ring selected from the group consisting of pyrrolidine, pyrrolidin-2-one, piperidine and morpholine, wherein the nitrogen atom of the N-heterocyclic ring is substituted by a substituent selected from the group consisting of:
 (1) lower alkyl,
 (2) cycloalkyl,
 (3) lower phenylalkyl,
 (4) lower cyanoalkyl,
 (5) lower halogenalkyl,
 (6) lower alkoxyalkyl,
 (7) phenyl optionally substituted by one to three substituents selected from the group consisting of lower alkyl, lower alkoxy, lower halogenalkyl and halogen, and
 (8) —$COOR^{11}$; wherein $R^{11}$ is lower alkyl;
(g) m is 2 or 3, and
(h) n is 0, 1, 2 or 3.

2. A compound of claim 1, wherein $R^4$ is —$(CR^9R^{10})_n$-heterocyclyl.

3. A compound of claim 1, wherein $R^4$ is —$(CR^9R^{10})_n$-heterocyclyl wherein said heterocyclyl is pyrrolidine or pyrrolidin-2-one.

4. A compound of claim 1 wherein $R^4$ is —$(CR^9R^{10})_n$-heterocyclyl wherein said heterocyclyl is pyrrolidin-3-yl.

5. A compound of claim 1, wherein $R^4$ is —$(CR^9R^{10})_n$-heterocyclyl wherein said heterocyclyl is piperidine or morpholine.

6. A compound of claim 1, wherein $R^4$ is —$(CR^9R^{10})_n$-heterocyclyl wherein said heterocyclyl is piperidin-3-yl.

7. A compound of claim 1 wherein $R^4$ is —$(CR^9R^{10})_n$-heterocyclyl wherein said heterocyclyl is morpholine.

8. A compound of claim 1 wherein $R^9$ and $R^{10}$ are hydrogen.

9. A compound of claim 1 wherein n is 0 or 1.

10. A compound of claim 1, wherein $R^4$ is —$(CR^5R^6)_m$—$NR^7R^8$ and wherein m is 2 or 3.

11. A compound of claim 1 wherein $R^4$ is —$(CR^5R^6)_m$—$NR^7R^8$ and wherein $R^7$ and $R^8$ independently from each other are selected from the group consisting of:
(1) lower alkyl,
(2) phenyl optionally substituted by lower alkyl,
(3) lower phenylalkyl, and
(4) lower hydroxyalkyl.

12. A compound of claim 1 wherein $R^4$ is —$(CR^5R^6)_m$—$NR^7R^8$ and wherein:
(a) $R^5$ and $R^6$ are hydrogen; and
(b) $R^7$ and $R^8$ together with the nitrogen atom to which they are attached form a 3-, 4-, 5-, 6- or 7-membered saturated heterocyclic ring optionally containing a further heteroatom of oxygen or sulfur, said heterocyclic ring being unsubstituted or substituted by lower alkyl.

13. A compound of claim 1 wherein $R^4$ is —$(CR^5R^6)_m$—$NR^7R^8$ and wherein:
(a) $R^5$ and $R^6$ are hydrogen; and
(b) $R^7$ and $R^8$ together with the nitrogen atom to which they are attached form a heterocyclic ring selected from the group consisting of:

(1) aziridine,
(2) azetidine,
(3) pyrrolidine,
(4) piperidine,
(5) azepane,
(6) morpholine, and
(7) thiomorpholine;
said heterocyclic ring being unsubstituted or substituted by lower alkyl.

14. A compound of claim 1 wherein $R^4$ is —$(CR^5R^6)_m$—$NR^7R^8$ and wherein:
(a) m is 2;
(b) $R^5$ and $R^6$ are hydrogen; and
(c) $R^7$ and $R^8$ together with the nitrogen atom to which they are attached form a heterocyclic ring selected from the group consisting of pyrrolidine, piperidine and azepane.

15. A compound of claim 1 wherein $R^1$ is lower alkyl.
16. A compound of claim 1 wherein $R^1$ is isopropyl or tert-butyl.
17. A compound of claim 1 wherein $R^1$ is cycloalkyl.
18. A compound of claim 1 wherein $R^1$ is lower alkyl, $R^2$ is hydrogen, and $R^3$ is hydrogen.
19. A compound of claim 1 wherein $R^1$ is cycloalkyl, $R^2$ is hydrogen, and $R^3$ is hydrogen.
20. A compound according to claim 1, selected from the group consisting of:
(4-isopropyl-piperazin-1-yl)-[1-(1-isopropyl-pyrrolidin-3-yl)-1H-indol-5-yl]-methanone;
(4-cyclopentyl-piperazin-1-yl)-[1-(1-ethyl-pyrrolidin-3-yl)-1H-indol-5-yl]-methanone;
(4-cyclopentyl-piperazin-1-yl)-[1-(1-isopropyl-pyrrolidin-3-yl)-1H-indol-5-yl]-methanone;
[1-(1-ethyl-piperidin-3-ylmethyl)-1H-indol-5-yl]-(4-sopropyl-piperazin-1-yl)-methanone;
(4-cyclobutyl-piperazin-1-yl)-[1-(1-ethyl-pyrrolidin-3-yl)-1H-indol-5-yl]-methanone;
(4-cyclobutyl-piperazin-1-yl)-[1-(1-isopropyl-pyrrolidin-3-yl)-1H-indol-5-yl]-methanone;
[1-(1-benzyl-piperidin-3-ylmethyl)-1H-indol-5-yl]-(4-cyclobutyl-piperazin-1-yl)-methanone;
[1-((S)-1-benzyl-pyrrolidin-2-ylmethyl)-1H-indol-5-yl]-(4-isopropyl-piperazin-1-yl)-methanone;
[1-(1-benzyl-piperidin-3-yl)-1H-indol-5-yl]-(4-isopropyl-piperazin-1-yl)-methanone; and
any pharmaceutically acceptable salt thereof.

21. A compound according to claim 1, selected from the group consisting of:
[1-((S)-1-benzyl-pyrrolidin-2-ylmethyl)-1H-indol-5-yl]-(4-cyclopentyl-piperazin-1-yl)-methanone;
(4-isopropyl-piperazin-1-yl)-[1-(1-methyl-piperidin-3-yl)-1H-indol-5-yl]-methanone;
(4-cyclopentyl-piperazin-1-yl)-{1-[2-(1-methyl-piperidin-2-yl)-ethyl]-1H-indol-5-yl}-methanone;
[1-(2-azepan-1-yl-ethyl)-1H-indol-5-yl]-(4-isopropyl-piperazin-1-yl)-methanone;
(4-cyclopentyl-piperazin-1-yl)-[1-(2-pyrrolidin-1-yl-ethyl)-1H-indol-5-yl]-methanone;
(4-cyclopentyl-piperazin-1-yl)-[1-(2-piperidin-1-yl-ethyl)-1H-indol-5-yl]-methanone;
[1-(2-azepan-1-yl-ethyl)-1H-indol-5-yl]-(4-cyclopentyl-piperazin-1-yl)-methanone;
(4-cyclopentyl-piperazin-1-yl)-[1-(2-dimethylamino-2-methyl-propyl)-1H-indol-5-yl]-methanone;
[1-(1-ethyl-piperidin-3-yl)-2-methyl-1H-indol-5-yl]-(4-isopropyl-piperazin-1-yl)-methanone;
[1-((S)-1-cyclopentyl-pyrrolidin-3-yl)-1H-indol-5-yl]-(4-isopropyl-piperazin-1-yl)-methanone;
and any pharmaceutically acceptable salt thereof.

22. A process for the manufacture of a compound according to claim 1 which process comprises:
(a) reacting a compound of formula II:

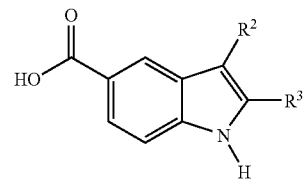

wherein $R^2$ and $R^3$ are as defined in claim 1,
with a piperazine of formula III:

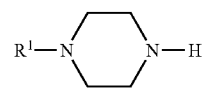

wherein $R^1$ as defined in claim 1,
in the presence of a coupling reagent under basic conditions to obtain a compound of formula IV:

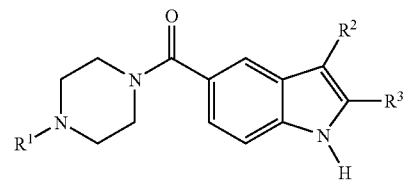

wherein $R^1$, $R^2$ and $R^3$ are as defined in claim 1, and
(b) chemically converting the compound of formula IV into a compound of formula I:

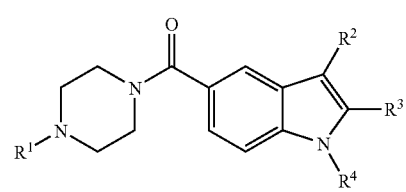

wherein $R^4$ is a group as defined in claim 1, and
(c) optionally converting the compound of formula I into a pharmaceutically acceptable acid addition salt.

23. A pharmaceutical composition comprising a therapeutically effective amount of a compound of claim 1 and a pharmaceutically acceptable carrier.

* * * * *